United States Patent
Hong et al.

(10) Patent No.: US 12,291,525 B2
(45) Date of Patent: May 6, 2025

(54) PROCESS FOR SYNTHESIS OF A 2-(5-ISOXAZOLYL)-PHENOL

(71) Applicant: FMC Corporation, Philadelphia, PA (US)

(72) Inventors: Junbae Hong, Newark, DE (US); Joerg Bruening, Wilmington, DE (US)

(73) Assignee: FMC Corporation, Philadelphia, PA (US)

( * ) Notice: Subject to any disclaimer, the term of this patent is extended or adjusted under 35 U.S.C. 154(b) by 525 days.

(21) Appl. No.: 17/781,777

(22) PCT Filed: Dec. 2, 2020

(86) PCT No.: PCT/US2020/062782
§ 371 (c)(1),
(2) Date: Jun. 2, 2022

(87) PCT Pub. No.: WO2021/113284
PCT Pub. Date: Jun. 10, 2021

(65) Prior Publication Data
US 2023/0061554 A1 Mar. 2, 2023

Related U.S. Application Data

(60) Provisional application No. 62/942,504, filed on Dec. 2, 2019.

(51) Int. Cl.
C07D 413/12 (2006.01)
C07D 239/38 (2006.01)
C07D 261/08 (2006.01)

(52) U.S. Cl.
CPC ......... C07D 413/12 (2013.01); C07D 239/38 (2013.01); C07D 261/08 (2013.01)

(58) Field of Classification Search
CPC ... C07D 413/12; C07D 239/38; C07D 261/08
USPC ....................................................... 544/315
See application file for complete search history.

(56) References Cited

FOREIGN PATENT DOCUMENTS

| | | |
|---|---|---|
| CN | 102140087 A | 8/2011 |
| CN | 105523911 A | 4/2016 |
| WO | 2015/108779 | 7/2015 |

OTHER PUBLICATIONS

Zhao et al., "Transition-Metal-Free Intramolecular Ullmann-Type O-Arylation: Synthesis of Chromone Derivatives", Agnewandte Chemie International Edition, 2011, vol. 50, p. 3769-3773.
Davies et al., Preparation of 2-chloro-1,3 Bis(dimethylamino) Trimethinium Hexafluorophosphate [[Methanaminium, N-[2-chloro-3-(dimethylamino)-2-propenylidene]-N-methyl-, hexafluorophosphate(1-)]], Organic Syntheses, vol. 80, p. 200-206 (2003).
Palucki et al., "Profiling the Formation of 2-Chloro-N,N-dimetylamino Trimethinium Chloride Salt, a Key Intermediate in the Manufacturing Process of Etoricoxib", Organic Process Research & Development, vol. 9, No. 2, 2005, p. 141-148.
Maltsev et al., "Synthesis of Soai Type 2-Arylpyrimidine-5-carbaldehydes through Desulfurative Cross-Coupling with Arylboronic Acids", European Journal of Organic Chemistry, 2014, p. 7426-7432.
Ye et al., "Synthesis and characterization of the titanium complexes bearing two β-enaminoketonato ligands with electron withdrawing groups/modified phenyls and their behaviors for ethylene (co-)polymerization", Dalton Transactions, vol. 39, No. 38, 2010, p. 9000-9007.
Stevenson et al., "An SAR study of hydroxy-trifluoromethylpyrazolines as inhibitors of Orai1-mediated store operated Ca2+ entry in MDA-MB-231 breast cancer cells using a convenient Fluorescence Imaging Plate Reader assay", Bioorganic & Medicinal Chemistry, vol. 26, No. 12, 2018, p. 3406-3413.
International Search Report of corresponding International Application No. PCT/US2020/062782, 2021.

(Continued)

Primary Examiner — Kristin A Vajda
(74) Attorney, Agent, or Firm — FMC Corporation

(57) ABSTRACT

A method for preparing a compound of Formula (1) and compounds therefrom, comprising treating a compound of Formula (2) to provide a compound of Formula (5) and treating the compound of Formula (5) with a hydroxylamine salt wherein $R^1$, $R^2$ and m are as defined in the specification. The compound of Formula (1), prepared by the above method, can be used to prepare a compound of Formula (8) wherein $R^1$, $R^2$, $R^3$ and m are as defined in the specification.

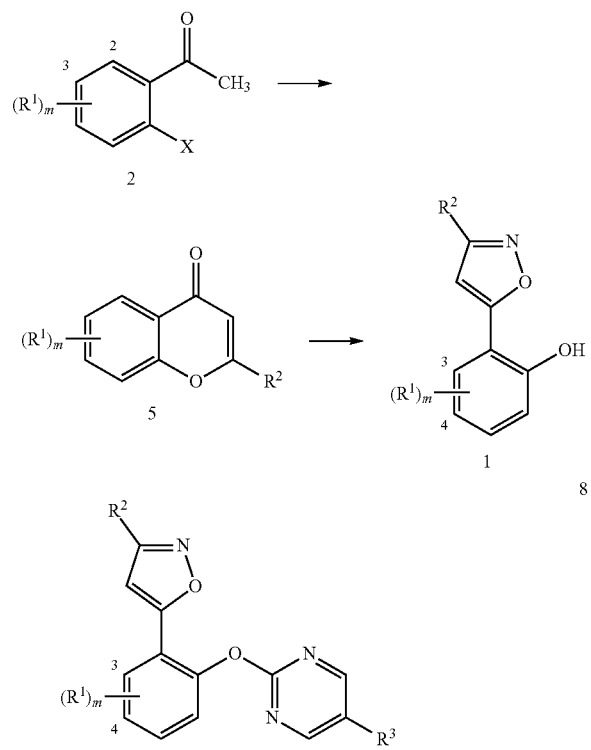

20 Claims, No Drawings

(56) References Cited

OTHER PUBLICATIONS

STN Search Report, available in the product catalog provided by Ukrorgsyntez Ltd., Database Registry (online), CAS No. 2007799-37-1; 1996870-48-4; 1995514-04-9; 1538084-85-3; 1039923-34-6; 1877844-63-7; 2023378-71-2; 2007709-51-3; 2006207-12-9, 2023.
Yamanaka, et al., "Preparation of Novel β-Trifluoromethyl Vinamidinium Salt and Its Synthetic Application to Trifluoromethylated Heterocycles", Tetrahedron Letters, vol. 37, No. 11, pp. 1829-1832, 1996.
Xie, et al.; "Green Synthesis of 4,6-Dimethyl-2-(methylsulfonyl) pyrimidine", Chemical Bulletin, vol. 73, No. 8, pp. 742-745, 2010.

PROCESS FOR SYNTHESIS OF A 2-(5-ISOXAZOLYL)-PHENOL

FIELD OF THE INVENTION

This invention relates to a method for preparing 2-(5-isoxazolyl)-phenol and compounds therefrom.

BACKGROUND OF THE INVENTION

Methods of preparing certain pyrimidinyloxy benzene derivatives as herbicides are described in WO 2015/108779. Methods for preparing pyrimidine derivatives are disclosed in *Organic Synthesis* 2003, 80, 200-206; *Organic Process Research and Development* 2005, 9, 141-148 and *Eur. J. Org. Chem.* 2014, 7426-7432. While methods disclosed in the preceding references can provide the desired compounds, continuous improvement is sought, particularly in the development of methods to provide materials on a commercial scale. Therefore, the need continues for new methods that are less costly, more efficient, more flexible, or more convenient to operate

SUMMARY OF THE INVENTION

Embodiment A. This invention is directed to a method for preparing a compound of Formula 1,

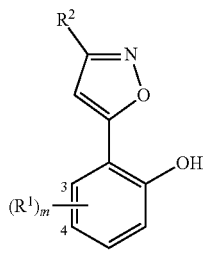

wherein
each $R^1$ is independently halogen, cyano, $C_1$-$C_4$ alkyl or $C_1$-$C_4$ haloalkyl;
$R^2$ is cyano, $C_1$-$C_4$ alkyl or $C_1$-$C_4$ haloalkyl; and
m is 0, 1, 2 or 3;
the method comprising
treating a compound of Formula 2

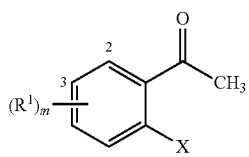

wherein
each $R^1$ is independently halogen, cyano, $C_1$-$C_4$ alkyl or $C_1$-$C_4$ haloalkyl;
m is 0, 1, 2 or 3; and
X is halogen;
with a compound of Formula 3

$$R^2(C=O)LG \qquad 3$$

wherein
$R^2$ is cyano, $C_1$-$C_4$ alkyl or $C_1$-$C_4$ haloalkyl; and
LG is chloro, $C_1$-$C_4$ alkoxy or —O(C=O)$R^2$ in the presence of an alkali metal base to provide a compound of Formula 4 or an alkali metal salt thereof

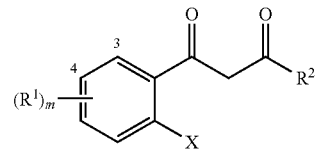

wherein
each $R^1$ is independently halogen, cyano, $C_1$-$C_4$ alkyl or $C_1$-$C_4$ haloalkyl;
$R^2$ is cyano, $C_1$-$C_4$ alkyl or $C_1$-$C_4$ haloalkyl;
m is 0, 1, 2 or 3; and
X is halogen;
heating the compound of Formula 4 or the alkali metal salt thereof to provide a compound of Formula 5

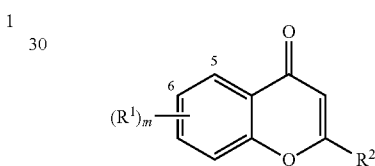

wherein
each $R^1$ is independently halogen, cyano, $C_1$-$C_4$ alkyl or $C_1$-$C_4$ haloalkyl;
$R^2$ is cyano, $C_1$-$C_4$ alkyl or $C_1$-$C_4$ haloalkyl; and
m is 0, 1, 2 or 3;
treating the compound of Formula 5 with a hydroxylamine salt to provide a compound of Formula 6

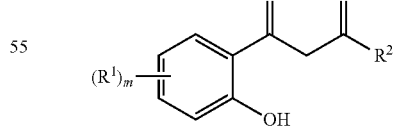

wherein
each $R^1$ is independently halogen, cyano, $C_1$-$C_4$ alkyl or $C_1$-$C_4$ haloalkyl;
$R^2$ is cyano, $C_1$-$C_4$ alkyl or $C_1$-$C_4$ haloalkyl; and
m is 0, 1, 2 or 3; and
treating the compound of Formula 6 with acid.

Embodiment B. This invention is also directed to a method for preparing a compound of Formula 8

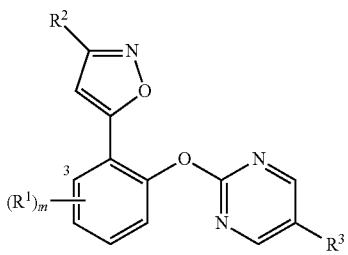

wherein
each $R^1$ is independently halogen, cyano, $C_1$-$C_4$ alkyl or $C_1$-$C_4$ haloalkyl;
$R^2$ is cyano, $C_1$-$C_4$ alkyl or $C_1$-$C_4$ haloalkyl;
$R^3$ is halogen, $C_1$-$C_4$ alkyl or $C_1$-$C_4$ haloalkyl; and
m is 0, 1, 2 or 3;
the method comprising
treating a compound of Formula 2

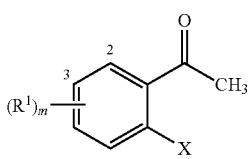

wherein
each $R^1$ is independently halogen, cyano, $C_1$-$C_4$ alkyl or $C_1$-$C_4$ haloalkyl;
m is 0, 1, 2 or 3; and
X is halogen;
with a compound of Formula 3

$R^2(C=O)LG$    3 wherein
$R^2$ is cyano, $C_1$-$C_4$ alkyl or $C_1$-$C_4$ haloalkyl; and
LG is chloro, $C_1$-$C_4$ alkoxy or —O(C=O)$R^2$
in the presence of an alkali metal base to provide a compound of Formula 4 or an alkali metal salt thereof

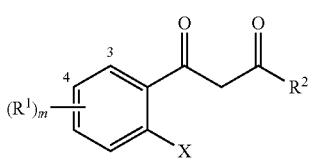

wherein
each $R^1$ is independently halogen, cyano, $C_1$-$C_4$ alkyl or $C_1$-$C_4$ haloalkyl;
$R^2$ is cyano, $C_1$-$C_4$ alkyl or $C_1$-$C_4$ haloalkyl;
m is 0, 1, 2 or 3; and
X is halogen;

heating the compound of Formula 4 or the alkali metal salt thereof to provide a compound of Formula 5

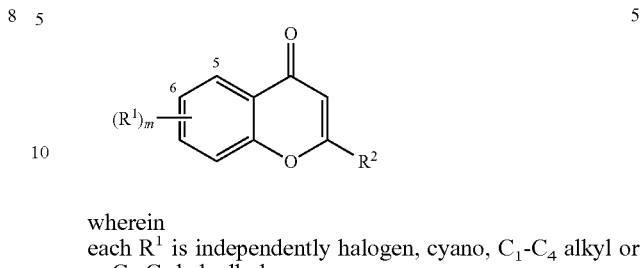

wherein
each $R^1$ is independently halogen, cyano, $C_1$-$C_4$ alkyl or $C_1$-$C_4$ haloalkyl;
$R^2$ is cyano, $C_1$-$C_4$ alkyl or $C_1$-$C_4$ haloalkyl; and
m is 0, 1, 2 or 3;
treating the compound of Formula 5 with a hydroxylamine salt to provide a compound of Formula 6

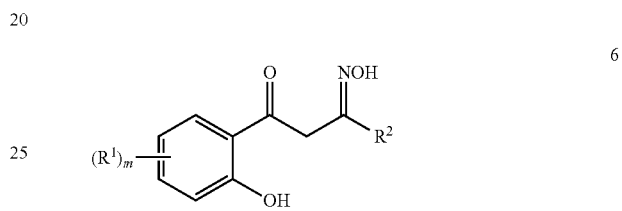

wherein
each $R^1$ is independently halogen, cyano, $C_1$-$C_4$ alkyl or $C_1$-$C_4$ haloalkyl;
$R^2$ is cyano, $C_1$-$C_4$ alkyl or $C_1$-$C_4$ haloalkyl; and
m is 0, 1, 2 or 3;
treating the compound of Formula 6 with acid to provide a compound of Formula 1

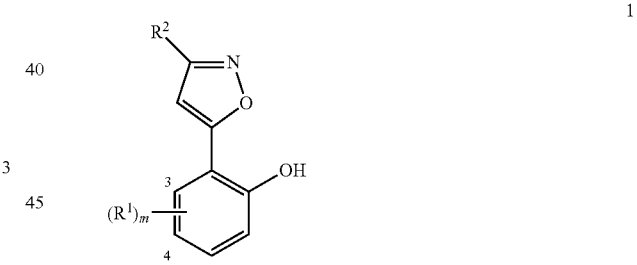

wherein
each $R^1$ is independently halogen, cyano, $C_1$-$C_4$ alkyl or $C_1$-$C_4$ haloalkyl;
$R^2$ is cyano, $C_1$-$C_4$ alkyl or $C_1$-$C_4$ haloalkyl; and
m is 0, 1, 2 or 3; and
treating the compound of Formula 1 in the presence of a second base with a compound of Formula 7

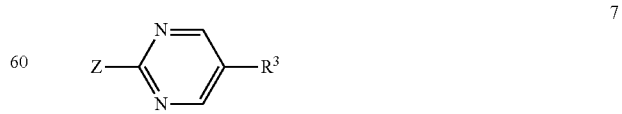

wherein
Z is halogen or $SO_2R^4$;
$R^3$ is halogen, $C_1$-$C_4$ alkyl or $C_1$-$C_4$ haloalkyl; and
$R^4$ is $C_1$-$C_4$ alkyl.

Embodiment C. This invention is also directed to a method for preparing a compound of Formula 5

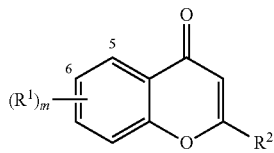

5 wherein
each $R^1$ is independently halogen, cyano, $C_1$-$C_4$ alkyl or $C_1$-$C_4$ haloalkyl;
$R^2$ is $C_1$-$C_4$ haloalkyl; and
m is 0, 1, 2 or 3; the method comprising
treating a compound of Formula 2

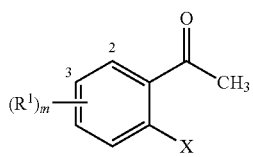

2 wherein
each $R^1$ is independently halogen, cyano, $C_1$-$C_4$ alkyl or $C_1$-$C_4$ haloalkyl;
m is 0, 1, 2 or 3; and
X is halogen;
with a compound of Formula 3A

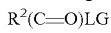 3A wherein
$R^2$ is $C_1$-$C_4$ haloalkyl; and
LG is chloro, $C_1$-$C_4$ alkoxy or —O(C=O)$R^2$
in the presence of an alkali metal base to provide a compound of Formula 4 or an alkali metal salt thereof

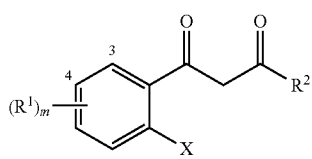

4A wherein
each $R^1$ is independently halogen, cyano, $C_1$-$C_4$ alkyl or $C_1$-$C_4$ haloalkyl;
$R^2$ is $C_1$-$C_4$ haloalkyl;
m is 0, 1, 2 or 3; and
X is halogen; and
heating the compound of Formula 4A or the alkali metal salt thereof.

Embodiment D. This invention is also directed to a compound of Formula 5A

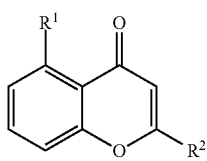

5A wherein
$R^1$ is halogen, cyano, $C_1$-$C_4$ alkyl or $C_1$-$C_4$ haloalkyl; and
$R^2$ is $C_1$-$C_2$ haloalkyl; wherein when $R^1$ is fluoro, $R^2$ is other than trifluoromethyl.

Embodiment E. This invention is also directed to a compound of Formula 4A or an alkali metal salt thereof

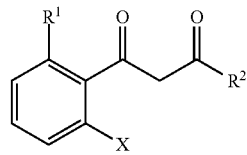

4A wherein
$R^1$ is halogen, cyano, $C_1$-$C_4$ alkyl or $C_1$-$C_4$ haloalkyl;
$R^2$ is $C_1$-$C_2$ haloalkyl; and
X is halogen; wherein when $R^1$ is fluoro, $R^2$ is other than trifluoromethyl.

Embodiment F. The method of Embodiment B wherein the compound of Formula 7 is prepared by
treating a compound of Formula 10

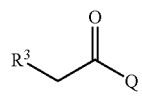

10 wherein
$R^3$ is halogen, $C_1$-$C_4$ alkyl or $C_1$-$C_4$ haloalkyl; and
Q is Cl or OH
in the presence of a halogenating agent and a compound of Formula 11

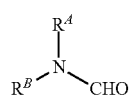

11 wherein
$R^A$ and $R^B$ are each independently $C_1$-$C_4$ alkyl; or
$R^A$ and $R^B$ are taken together to be —(CH$_2$)$_4$—, —(CH$_2$)$_5$— or —CH$_2$CH$_2$OCH$_2$CH$_2$—
to provide an intermediate of Formula 12

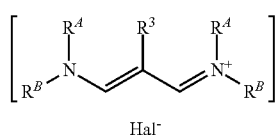

12 wherein
$R^3$ is halogen, $C_1$-$C_4$ alkyl or $C_1$-$C_4$ haloalkyl; and
$R^A$ and $R^B$ are each independently $C_1$-$C_4$ alkyl; or
$R^A$ and $R^B$ are taken together to be —(CH$_2$)$_4$—, —(CH$_2$)$_5$— or —CH$_2$CH$_2$OCH$_2$CH$_2$—; and
Hal$^-$ is chloride or bromide ion;

treating the intermediate of Formula 12 with an acid salt of a compound of Formula 13

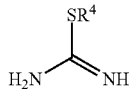

wherein
R$^4$ is C$_1$-C$_4$ alkyl
in the presence of a base to provide a compound of Formula 14

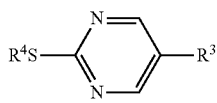

wherein
R$^3$ is halogen, C$_1$-C$_4$ alkyl or C$_1$-C$_4$ haloalkyl;
R$^4$ is C$_1$-C$_4$ alkyl; and
treating the compound of Formula 14 with an oxidant.

DETAILED DESCRIPTION OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, process or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used herein, the term "suitable" indicates that the entity or condition so described is appropriate for use in the situation or circumstance indicated. As used herein, the terms "treatment" or treating" denotes using a chemical or chemical process to alter the existing condition of other materials, chemicals or compounds. The terms "converting," "converted", conversion and related words refer to causing an entity such as a chemical compound to change in structure, form, character or function. For example, a compound of a first formula or structure is converted to a compound of a second formula or structure by a chemical process involving one or more treatments as defined above.

As used herein, the term "intermediate" refers to a compound or chemical entity in a chemical process that is prepared in a step after the starting material is provided and before the final product is prepared. In some instances, an intermediate is not isolated during the chemical process and is converted to a subsequent compound in situ. A set of brackets surrounding the chemical structure of an intermediate may be used herein to indicate that the intermediate is not isolated prior to its conversion to a subsequent compound; e.g. "[intermediate]".

As used herein, the term "telescopic" refers to a process in which at least one intermediate compound formed in the process is treated in a subsequent step of the process without its isolation. For example, a compound may be subjected to successive chemical reactions in just one reactor.

In the above recitations, the term "alkyl", used either alone or in compound words such as "alkylthio" or "haloalkyl" includes straight-chain or branched alkyl, such as methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include CH$_3$OCH$_2$, CH$_3$OCH$_2$CH$_2$, CH$_3$CH$_2$OCH$_2$, CH$_3$CH$_2$CH$_2$OCH$_2$ and CH$_3$CH$_2$OCH$_2$CH$_2$. "Alkylthio" includes branched or straight-chain alkylthio moieties such as methylthio, ethylthio, and the different propylthio, butylthio, pentylthio and hexylthio isomers.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include CHF$_2$, F$_3$C, ClCH$_2$, CF$_3$CH$_2$ and CF$_3$CCl$_2$.

The terms "haloalkoxy", and the like, is defined analogously to the term "haloalkyl". Examples of "haloalkoxy" include CF$_3$O—, CCl$_3$CH$_2$O—, HCF$_2$CH$_2$CH$_2$O— and CF$_3$CH$_2$O—. "Alkylcarbonyl" denotes a straight-chain or branched alkyl moieties bonded to a C(=O) moiety. Examples of "alkylcarbonyl" include CH$_3$C(=O)—, CH$_3$CH$_2$CH$_2$C(=O)— and (CH$_3$)$_2$CHC(=O)—. Examples of "alkoxycarbonyl" include CH$_3$OC(=O)—, CH$_3$CH$_2$OC(=O)—, CH$_3$CH$_2$CH$_2$OC(=O)—, (CH$_3$)$_2$CHOC(=O)— and the different butoxy- or pentoxycarbonyl isomers. "Alkylcarbonyloxy" denotes a straight-chain or branched alkyl moieties bonded to a C(=O)O— moiety. Examples of "alkylcarbonyloxy" include CH$_3$C(=O)O—, CH$_3$CH$_2$CH$_2$C(=O)O— and (CH$_3$)$_2$CHC(=O)O—.

The total number of carbon atoms in a substituent group is indicated by the "C$_i$-C$_j$" prefix where, for example, i and j are numbers from 1 to 4. For example, C$_1$-C$_4$ alkylsulfonyl designates methylsulfonyl through butylsulfonyl; C$_2$ alkoxyalkyl designates CH$_3$OCH$_2$—; C$_3$ alkoxyalkyl designates, for example, CH$_3$CH(OCH$_3$)—, CH$_3$OCH$_2$CH$_2$— or CH$_3$CH$_2$OCH$_2$—; and C$_4$ alkoxyalkyl designates the various isomers of an alkyl group substituted with an alkoxy group containing a total of four carbon atoms, examples including CH$_3$CH$_2$CH$_2$OCH$_2$— and CH$_3$CH$_2$OCH$_2$CH$_2$—.

When a compound is substituted with a substituent bearing a subscript that indicates the number of said substituents can exceed 1, said substituents (when they exceed 1) are independently selected from the group of defined substituents, (e.g., (R$^3$)$_m$, m is 0, 1, 2 or 3). When a group contains a substituent that can be hydrogen, for example (when m=0), then when this substituent is taken as hydrogen, it is recognized that this is equivalent to said group being unsubstituted. When a variable group is shown to be optionally attached to a position, (for example (R$^1$)$_m$) wherein m may be 0, then hydrogen may be at the position even if not recited in the variable group definition. When one or more positions on a group are said to be "not substituted" or "unsubstituted", then hydrogen atoms are attached to take up any free valency.

The term "optionally" when used herein means that the optional condition may or may not be present. For example, when a reaction is conducted optionally in the presence of a solvent, the solvent may or may not be present.

The term "optionally substituted" refers to groups which are unsubstituted or have at least one non-hydrogen substituent that does not extinguish the chemical or biological activity possessed by the unsubstituted analog. As used herein, the following definitions shall apply unless otherwise indicated. The term "optionally substituted with" is used interchangeably with the phrase "unsubstituted or substituted with" or with the term "(un)substituted with." Unless otherwise indicated, an optionally substituted group may have a substituent at each substitutable position of the group, and each substitution is independent of the other.

Embodiments of the invention include the following.

Embodiment A1. The method of Embodiment A wherein each R$^1$ is independently halogen or cyano.

Embodiment A2. The method of Embodiment A1 wherein each R$^1$ is independently halogen.

Embodiment A3. The method of Embodiment A2 wherein each R$^1$ is chlorine.

Embodiment A4. The method of Embodiment A2 wherein each R$^1$ is bromine.

Embodiment A5. The method of any of Embodiments A through A4 wherein m is 0, 1 or 2.

Embodiment A6. The method of Embodiment A5 wherein m is 1 or 2.

Embodiment A7. The method of Embodiment A6 wherein each R$^1$ is attached to the remainder of Formula 1 at the 3- or 4-position or both the 3- and 4-positions.

Embodiment A8. The method of Embodiment A7 wherein m is 1.

Embodiment A9. The method of Embodiment A8 wherein R$^1$ is attached to the remainder of Formula 1 at the 3-position.

Embodiment A10. The method of Embodiment A8 wherein R$^1$ is attached to the remainder of Formula 1 at the 4-position.

Embodiment A11. The method of any of Embodiments A6 through A10 wherein R$^1$ is chlorine.

Embodiment A12. The method of any of Embodiments A through A11 wherein R$^2$ is C$_1$-C$_4$ alkyl or C$_1$-C$_4$ haloalkyl.

Embodiment A13. The method of Embodiment A12 wherein R$^2$ is C$_1$-C$_4$ haloalkyl.

Embodiment A14. The method of Embodiment A13 wherein R$^2$ is C$_1$-C$_2$ fluoroalkyl.

Embodiment A15. The method of Embodiment A14 wherein R$^2$ is C$_1$ fluoroalkyl.

Embodiment A16. The method of Embodiment A15 wherein R$^2$ is CHF$_2$.

Embodiment A17. The method of any of Embodiments A through A16 wherein X is bromine or chlorine.

Embodiment A18. The method of Embodiment A17 wherein X is chlorine.

Embodiment A19. The method of any of Embodiments A through A18 wherein the compound of Formula 2 is prepared by treating a compound of Formula 9

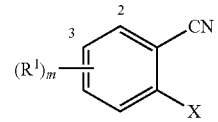

9 wherein each R$^1$ is independently halogen, C$_1$-C$_4$ alkyl or C$_1$-C$_4$ haloalkyl;

X is halogen; and m is 0, 1, 2 or 3;

with a methyl magnesium halide followed by treatment with water or aqueous acid.

Embodiment A20. The method of Embodiment A19 wherein each R$^1$ is independently halogen.

Embodiment A21. The method of Embodiment A20 wherein each R$^1$ is chlorine.

Embodiment A22. The method of Embodiment A20 wherein each R$^1$ is bromine.

Embodiment A23. The method of any of Embodiments A19 through A22 wherein m is 0, 1 or 2.

Embodiment A24. The method of Embodiment A23 wherein m is 1 or 2.

Embodiment A25. The method of Embodiment A24 wherein each R$^1$ is attached to the remainder of Formula 9 at the 2- or 3-position or both the 2- and 3-positions.

Embodiment A26. The method of Embodiment A24 wherein m is 1.

Embodiment A27. The method of Embodiment A26 wherein R$^1$ is attached to the remainder of Formula 9 at the 2-position.

Embodiment A28. The method of Embodiment A27 wherein R$^1$ is chlorine.

Embodiment A29. The method of any of Embodiments A19 through A28 wherein the methyl magnesium halide is methyl magnesium chloride.

Embodiment A30. The method of any of Embodiments A through A29 further comprising treating the compound of Formula 1 with a compound of Formula 7

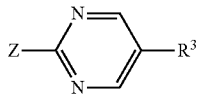

7 wherein
Z is halogen or $SO_2R^4$;
$R^3$ is halogen, $C_1$-$C_4$ alkyl or $C_1$-$C_4$ haloalkyl; and
$R^4$ is $C_1$-$C_4$ alkyl
in the presence of a second base to provide a compound of Formula 8

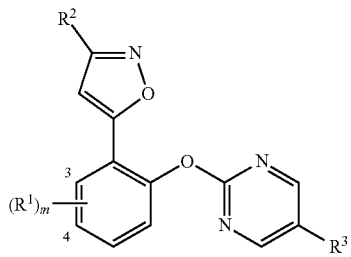

8 wherein
each $R^1$ is independently halogen, cyano, $C_1$-$C_4$ alkyl or $C_1$-$C_4$ haloalkyl;
$R^2$ is cyano, $C_1$-$C_4$ alkyl or $C_1$-$C_4$ haloalkyl;
$R^3$ is halogen, $C_1$-$C_4$ alkyl or $C_1$-$C_4$ haloalkyl; and
m is 0, 1, 2 or 3.

Embodiment A31. The method of Embodiment A30 wherein Z is chlorine.

Embodiment A32. The method of Embodiment A30 wherein Z is $SO_2R^4$.

Embodiment A33. The method of Embodiment A32 wherein $R^4$ is $C_1$-$C_2$ alkyl.

Embodiment A34. The method of Embodiment A33 wherein $R^4$ is methyl.

Embodiment A35. The method of any of Embodiments A30 through A34 wherein $R^3$ is halogen.

Embodiment A36. The method of Embodiment A35 wherein $R^3$ is chlorine.

Embodiment A37. The method of any of Embodiments A30 through A36 wherein the compound of Formula 8 is selected from the group consisting of
2-[2-(3-bromo-5-isoxazolyl)phenoxy]-5-chloropyrimidine,
5-chloro-2-[2-[3-(difluoromethyl)-5-isoxazolyl]phenoxy]pyrimidine,
5-chloro-2-[2-[3-(trifluoromethyl)-5-isoxazolyl]phenoxy]pyrimidine,
5-chloro-2-[2-[3-(difluoromethyl)-5-isoxazolyl]-3-fluorophenoxy]pyrimidine,
5-bromo-2-[2-[3-(difluoromethyl)-5-isoxazolyl]-3-fluorophenoxy]pyrimidine,
5-chloro-2-[2-[3-(trifluoromethyl)-5-isoxazolyl]-3-chlorophenoxy]pyrimidine,
5-chloro-2-[2-[3-(trifluoromethyl)-5-isoxazolyl]-3-fluorophenoxy]pyrimidine,
5-chloro-2-[2-[3-(difluoromethyl)-5-isoxazolyl]-3-chlorophenoxy]pyrimidine,
5-bromo-2-[2-[3-(difluoromethyl)-5-isoxazolyl]-3-chlorophenoxy]pyrimidine,
5-bromo-2-[2-[3-(trifluoromethyl)-5-isoxazolyl]-3-chlorophenoxy]pyrimidine and
5-chloro-2-[2-[3-(difluoromethyl)-5-isoxazolyl]-3-bromophenoxy]pyrimidine.

Embodiment A38. The method of A37 wherein the compound of Formula 8 is the compound of Formula 8A

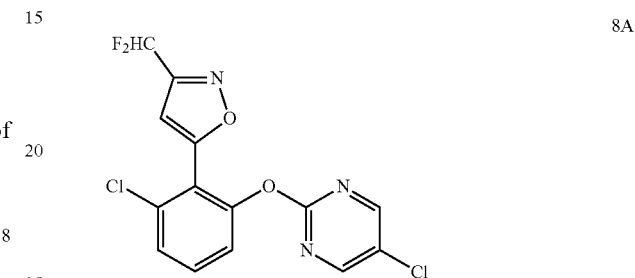

8A i.e. 5-chloro-2-[2-[3-(difluoromethyl)-5-isoxazolyl]-3-chlorophenoxy]pyrimidine (alternatively named 5-chloro-2-[3-chloro-2-[3-(difluoromethyl)-5-isoxazolyl]-phenoxy]-pyrimidine; CAS Number 1801862-02-1)

Embodiment B1. The method of Embodiment B wherein each $R^1$ is independently halogen or cyano.

Embodiment B2. The method of Embodiment B1 wherein each $R^1$ is independently halogen.

Embodiment B3. The method of Embodiment B2 wherein each $R^1$ is chlorine.

Embodiment B4. The method of Embodiment B3 wherein each $R^1$ is bromine.

Embodiment B5. The method of any of Embodiments B through B4 wherein m is 0, 1 or 2.

Embodiment B6. The method of Embodiment B5 wherein m is 1 or 2.

Embodiment B7. The method of Embodiment B6 wherein each $R^1$ is attached to the remainder of Formula 8 at the 3- or 4-position or both the 3- and 4-positions.

Embodiment B8. The method of Embodiment B6 wherein m is 1.

Embodiment B9. The method of Embodiment B8 wherein $R^1$ is attached to the remainder of Formula 8 at the 3-position.

Embodiment B10. The method of Embodiment B8 wherein $R^1$ is attached to the remainder of Formula 1 at the 4-position.

Embodiment B11. The method of any of Embodiments B6 through B10 wherein $R^1$ is chlorine.

Embodiment B12. The method of any of Embodiments B through B11 wherein $R^2$ is $C_1$-$C_4$ alkyl or $C_1$-$C_4$ haloalkyl.

Embodiment B13. The method of Embodiment B12 wherein $R^2$ is $C_1$-$C_4$ haloalkyl.

Embodiment B14. The method of Embodiment B13 wherein $R^2$ is $C_1$-$C_2$ fluoroalkyl.

Embodiment B15. The method of Embodiment B14 wherein $R^2$ is $C_1$ fluoroalkyl.

Embodiment B16. The method of Embodiment B15 wherein $R^2$ is $CHF_2$.

Embodiment B17. The method of any of Embodiments B through B16 wherein X is bromine or chlorine.

Embodiment B18. The method of Embodiment B17 wherein X is chlorine.

Embodiment B19. The method of any of Embodiments B through B18 wherein the compound of Formula 2 is prepared by treating a compound of Formula 9

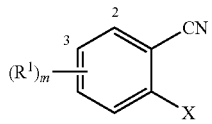

wherein
each $R^1$ is independently halogen, $C_1$-$C_4$ alkyl or $C_1$-$C_4$ haloalkyl;
X is halogen;
and
m is 0, 1, 2 or 3;
with a methyl magnesium halide followed by treatment with water or aqueous acid.

Embodiment B20. The method of Embodiment B19 wherein each $R^1$ is independently halogen.

Embodiment B21. The method of Embodiment B20 wherein each $R^1$ is chlorine.

Embodiment B22. The method of Embodiment B20 wherein each $R^1$ is bromine.

Embodiment B23. The method of any of Embodiments B19 through B22 wherein m is 0, 1 or 2.

Embodiment B24. The method of Embodiment B23 wherein m is 1 or 2.

Embodiment B25. The method of Embodiment B24 wherein each $R^1$ is attached to the remainder of Formula 9 at the 2- or 3-position or both the 2- and 3-positions.

Embodiment B26. The method of Embodiment B24 wherein m is 1.

Embodiment B27. The method of Embodiment B26 wherein $R^1$ is attached to the remainder of Formula 9 at the 2-position.

Embodiment B28. The method of Embodiment B27 wherein $R^1$ is chlorine.

Embodiment B29. The method of any of Embodiments B19 through B28 wherein the methyl magnesium halide is methyl magnesium chloride.

Embodiment B30. The method of any of Embodiments B through B29 wherein Z is chlorine.

Embodiment B31. The method of any of Embodiments B through B29 wherein Z is $SO_2R^4$.

Embodiment B32. The method of Embodiment B31 wherein $R^4$ is $C_1$-$C_2$ alkyl.

Embodiment B33. The method of Embodiment B32 wherein $R^4$ is methyl.

Embodiment B34. The method of any of Embodiments B through B33 wherein $R^3$ is halogen.

Embodiment B35. The method of Embodiment B34 wherein $R^3$ is chlorine.

Embodiment B36. The method of any of Embodiments B through B35 wherein the compound of Formula 8 is selected from the group consisting of
2-[2-(3-bromo-5-isoxazolyl)phenoxy]-5-chloropyrimidine,
5-chloro-2-[2-[3-(difluoromethyl)-5-isoxazolyl]phenoxy]pyrimidine,
5-chloro-2-[2-[3-(trifluoromethyl)-5-isoxazolyl]phenoxy]pyrimidine,
5-chloro-2-[2-[3-(difluoromethyl)-5-isoxazolyl]-3-fluorophenoxy]pyrimidine,
5-bromo-2-[2-[3-(difluoromethyl)-5-isoxazolyl]-3-fluorophenoxy]pyrimidine,
5-chloro-2-[2-[3-(trifluoromethyl)-5-isoxazolyl]-3-chlorophenoxy]pyrimidine,
5-chloro-2-[2-[3-(trifluoromethyl)-5-isoxazolyl]-3-fluorophenoxy]pyrimidine,
5-chloro-2-[2-[3-(difluoromethyl)-5-isoxazolyl]-3-chlorophenoxy]pyrimidine,
5-bromo-2-[2-[3-(difluoromethyl)-5-isoxazolyl]-3-chlorophenoxy]pyrimidine,
5-bromo-2-[2-[3-(trifluoromethyl)-5-isoxazolyl]-3-chlorophenoxy]pyrimidine and
5-chloro-2-[2-[3-(difluoromethyl)-5-isoxazolyl]-3-bromophenoxy]pyrimidine.

Embodiment B37. The method of B36 wherein the compound of Formula 8 is the compound of Formula 8A

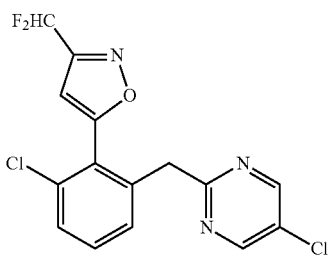

i.e. 5-chloro-2-[2-[3-(difluoromethyl)-5-isoxazolyl]-3-chlorophenoxy]pyrimidine (alternatively named 5-chloro-2-[3-chloro-2-[3-(difluoromethyl)-5-isoxazolyl]-phenoxy]-pyrimidine; CAS Number 1801862-02-1)

Embodiment C1. The method of Embodiment C wherein each $R^1$ is independently halogen or cyano.

Embodiment C2. The method of Embodiment C wherein each $R^1$ is independently halogen.

Embodiment C3. The method of Embodiment C2 wherein each $R^1$ is chlorine.

Embodiment C4. The method of Embodiment C2 wherein each $R^1$ is bromine.

Embodiment C5. The method of any of Embodiments C through C4 wherein m is 0, 1 or 2.

Embodiment C6. The method of Embodiment C5 wherein m is 1 or 2.

Embodiment C7. The method of Embodiment C6 wherein each $R^1$ is attached to the remainder of Formula 2 at the 2- or 3-position or both the 2- and 3-positions.

Embodiment C8. The method of Embodiment C6 wherein m is 1.

Embodiment C9. The method of Embodiment C8 wherein $R^1$ is attached to the remainder of Formula 2 at the 2-position.

Embodiment C10. The method of Embodiment C8 wherein $R^1$ is attached to the remainder of Formula 2 at the 3-position.

Embodiment C11. The method of any of Embodiments C6 through C10 wherein $R^1$ is chlorine.

Embodiment C12. The method of any of Embodiments C through C11 wherein the compound of Formula 2 is prepared by treating a compound of Formula 9

Embodiment C13. The method of any of Embodiments C through C13 wherein the compound of Formula 2 is prepared by treating a compound of Formula 9

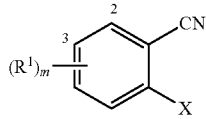

wherein
each $R^1$ is independently halogen, $C_1$-$C_4$ alkyl or $C_1$-$C_4$ haloalkyl;
X is halogen; and
m is 0, 1, 2 or 3;
with a methyl magnesium halide followed by treatment with water or aqueous acid.

Embodiment C14. The method of Embodiment C13 wherein each $R^1$ is independently halogen.

Embodiment C15. The method of Embodiment C14 wherein each $R^1$ is chlorine.

Embodiment C16. The method of Embodiment C15 wherein each $R^1$ is bromine.

Embodiment C17. The method of any of Embodiments C13 through C16 wherein m is 0, 1 or 2.

Embodiment C18. The method of Embodiment C17 wherein m is 1 or 2.

Embodiment C19. The method of Embodiment C18 wherein each $R^1$ is attached to the remainder of Formula 9 at the 2- or 3-position or both the 2- and 3-positions.

Embodiment C20. The method of Embodiment C18 wherein m is 1.

Embodiment C21. The method of Embodiment C20 wherein $R^1$ is attached to the remainder of Formula 9 at the 2-position.

Embodiment C22. The method of Embodiment C21 wherein $R^1$ is chlorine.

Embodiment C23. The method of any of Embodiments C13 through C22 wherein the methyl magnesium halide is methyl magnesium chloride.

Embodiment C24. The method of Embodiment C wherein the compound of Formula 5B

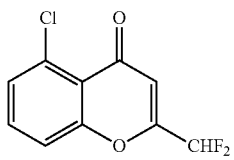

is prepared.

Embodiment D1. The compound of Embodiment D wherein $R^1$ is halogen or cyano.

Embodiment D2. The compound of Embodiment D1 wherein $R^1$ is halogen.

Embodiment D3. The compound of Embodiment D2 wherein $R^1$ is chlorine.

Embodiment D4. The compound of Embodiment D2 wherein $R^1$ is bromine.

Embodiment D5. The compound of any of Embodiments D through D4 wherein $R^2$ is $C_1$-$C_2$ fluoroalkyl.

Embodiment D6. The compound of Embodiment D5 wherein $R^2$ is $C_1$ fluoroalkyl.

Embodiment D7. The compound of Embodiment D6 wherein $R^2$ is $CHF_2$.

Embodiment D8. The compound of Embodiment D7 that is the compound of Formula 5B

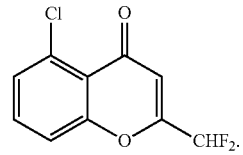

Embodiment E1. The compound of Embodiment E wherein $R^1$ is halogen or cyano.

Embodiment E2. The compound of Embodiment E1 wherein $R^1$ is cyano.

Embodiment E3. The compound of Embodiment E1 wherein $R^1$ is halogen.

Embodiment E4. The compound of Embodiment E3 wherein $R^1$ is chlorine.

Embodiment E5. The compound of Embodiment E3 wherein $R^1$ is bromine.

Embodiment E6. The compound of any of Embodiments E through E5 wherein X is bromine or chlorine.

Embodiment E7. The compound of Embodiment E6 wherein X is chlorine.

Embodiment E8. The compound of any of Embodiments E through E7 wherein $R^2$ is $C_1$-$C_2$ fluoroalkyl.

Embodiment E9. The compound of Embodiment E8 wherein $R^2$ is $C_1$ fluoroalkyl.

Embodiment E10. The compound of Embodiment E9 wherein $R^2$ is $CHF_2$.

Embodiment E11. The compound of any of Embodiments E through E10 that is the sodium salt, i.e. the compound of Formula 4B

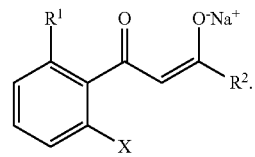

Embodiment E12. The compound of Embodiment E that is the compound of Formula 4C or its sodium salt

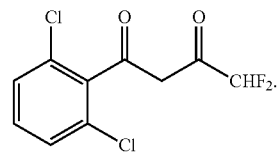

Embodiment F1. The method of Embodiment F wherein $R^4$ is $C_1$-$C_2$ alkyl.

Embodiment F2. The method of Embodiment F1 wherein $R^4$ is methyl.

Embodiment F3. The method of any of Embodiments F through F2 wherein $R^3$ is halogen.

Embodiment F4. The method of Embodiment F3 wherein $R^3$ is chlorine.

Embodiment F5. The method of any of Embodiments F through F4 wherein the halogenating agent is $POCl_3$.

Embodiment F5a. The method of Embodiment F5 wherein the halogenating agent is the Vilsmeier-Haack reagent.

Embodiment F6. The method of any Embodiments F through F5 wherein Q is Cl.

Embodiment F7. The method of any of Embodiments F through FC5 wherein Q is OH.

Embodiment F8. The method of any of Embodiments F through F7 wherein each $R^A$ and $R^B$ is independently $C_1$-$C_4$ alkyl.

Embodiment F9. The method of Embodiment F8 wherein each $R^A$ and $R^B$ is independently $C_1$-$C_2$ alkyl.

Embodiment F10. The method of Embodiment F9 wherein each $R^A$ and $R^B$ is methyl.

Embodiment F11. The method of any of Embodiments F through F10 wherein the salt of the compound of Formula 13 is the hemisulfate salt.

Embodiments of this invention, including Embodiments A through A38, B through B37, C through C24, D through D8, E through E12 and F through F11 above as well as any other embodiments described herein, can be combined in any manner, and the descriptions of variables in the embodiments pertain not only to the compounds of Formula 8 but also to the starting compounds and intermediate compounds of Formulae 1 through 7 and 9 through 14, useful for preparing the compounds of Formula 8.

Preferred Embodiments include the following.

Embodiment P1. The method of Embodiments A, B, or F wherein
$R^2$ is $C_1$-$C_4$ haloalkyl; and
m is 0, 1 or 2.

Embodiment P2. The method of Embodiment P1 wherein each $R^1$ is independently halogen or cyano; and
$R^2$ is $C_1$-$C_2$ fluoroalkyl.

Embodiment P3. The method of Embodiment P2 wherein
$R^1$ is halogen;
$R^2$ is $C_1$ fluoroalkyl;
m is 1; and
$R^1$ is attached to the remainder of Formula 1 at the 3-position.

Embodiment P4. The method of Embodiment P2 wherein
$R^1$ is chlorine; and
$R^2$ is $CHF_2$.

Embodiment P5. The method of any of Embodiments P1 through P4 wherein $R^3$ is chlorine.

Embodiment P6. The method of any of Embodiments P1 through P5 wherein Z is chlorine or $SO_2R^4$.

Embodiment P7. The method of Embodiment P6 wherein Z is $SO_2CH_3$.

Embodiment P8. The compound of Embodiments D or E wherein $R^2$ is $C_1$-$C_2$ fluoroalkyl.

Embodiment P9. The compound of Embodiment P8 wherein
$R^1$ is halogen; and
$R^2$ is $C_1$ fluoroalkyl.

Embodiment P10. The compound of Embodiment P9 wherein
$R^1$ is chlorine; and
$R^2$ is $CHF_2$.

In the following Schemes the definitions of X, $R^A$, $R^B$, $R^1$, $R^2$, $R^3$, $R^4$ and m in the compounds of Formulae 1 through 14 below are as defined above in the Summary of the Invention and description of embodiments unless otherwise indicated.

The methods described herein provide an efficient and robust synthesis of 2-(isoxazol-5-yl)-phenol of Formula 1 useful in the preparation of herbicidal compounds of Formula 8. Compounds of Formulae 1 and 8 have been prepared previously as described in WO2015/108779.

As shown in Scheme 1, a compound of Formula 1 can be prepared in a telescopic manner, which comprises treating a 4H-1-benzopyran-4-one of Formula 5 with a hydroxylamine salt, preferably hydroxylamine hydrochloride, in the presence of a base; and
treating the resulting 1-(2-hydroxyphenyl)-butane-1,3-dione 3-oxime of Formula 6 with acid. In some instances, the compound of Formula 6 can be treated with acid to provide cyclization of the isoxazole to form the compound of Formula 1 without isolation from the reaction mixture.

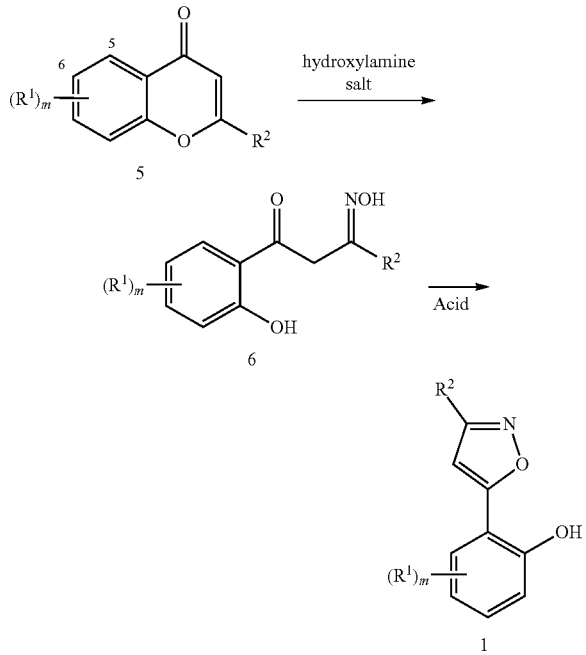

The compound of Formula 5 is prepared as shown in Scheme 2. Treatment of a compound of Formula 2 with an acylating agent LG(C=O)$R^2$ of Formula 3, wherein LG is chloro, alkoxy or —O(C=O)$R^2$, in the presence of an alkali metal base provides a compound of Formula 4 or an alkali metal salt thereof, a compound of Formula 4B. Suitable alkali metal bases for the reaction include alkali metal alkoxides such as sodium methoxide, sodium isopropoxide and potassium tert-butoxide; or alkali metal hydroxides such as potassium hydroxide and sodium hydroxide; or alkali metal carbonates and bicarbonates such as sodium bicarbonate, potassium bicarbonate, sodium carbonate, potassium carbonate and cesium carbonate. A preferred base is sodium methoxide. Suitable solvents include toluene, tetrahydrofuran, dimethyl sulfoxide, N,N-dimethylformamide or N,N-dimethylacetamide. A preferred solvent is N,N-dimethylacetamide. One of ordinary skill in the art will recognize that the compound of Formula 4B can exist in more than one tautomeric form, and any tautomeric form of the compound of Formula 4B is envisioned in this invention. For simplicity, only one tautomer is shown. Acidification of the reaction mixture allows for the isolation of the compound of Formula 4, if desired. Preferably, the compound of Formula 4 is not isolated, since the following step is facilitated by base.

The compound of Formula 4 or 4B can be cyclized with displacement of the ortho-halogen to provide a compound of Formula 5. In some embodiments, the compound of Formula 4B cyclizes to the compound of Formula 5 under the conditions of the acylation of the compound of Formula 2, and/or by further heating the compound of Formula 4B, for example at temperatures of about 100 to 200° C., or about 120 to about 180° C., or about 140 to about 160° C. In any of such embodiments, the compound of Formulae 4 or 4B does not need to be isolated. If the compound of Formula 4 is isolated from the first reaction mixture, addition of base may be needed to facilitate its cyclization to the compound of Formula 5. Alternatively, the reaction sequences shown in Schemes 1 and 2 could be carried out in a single reactor without isolating the compound of Formula 5.

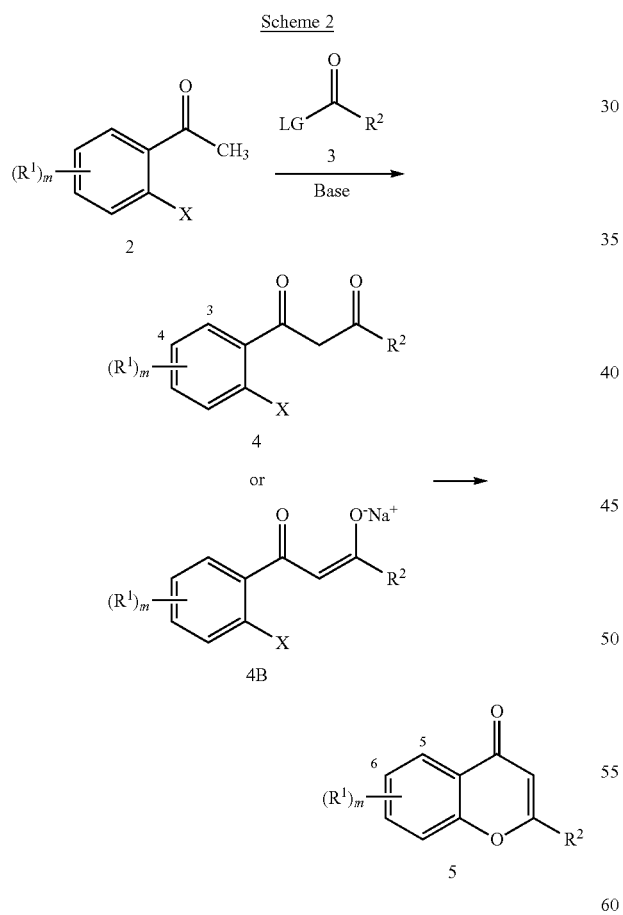

Treatment of a nitrile of Formula 9 with a methyl magnesium halide such as methyl magnesium chloride followed by hydrolysis can provide an ortho-halo acetophenone of Formula 2 as shown in Scheme 3. Notably X is chloro or bromo, and more notably chloro. In some instances, the compound of Formula 2 may be commercially available.

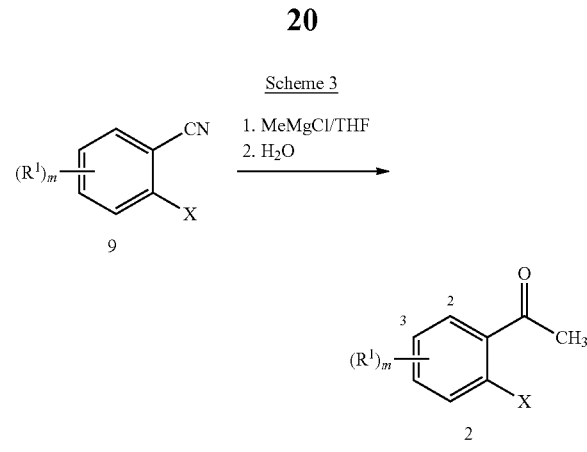

As shown in Scheme 4, this invention also relates to a method for preparing a compound of Formula 8 by coupling a pyrimidine of Formula 7A or 7B with a phenol of Formula 1, typically in the presence of a base and a solvent. Suitable solvents include acetonitrile, toluene, isopropanol, tetrahydrofuran, dimethyl sulfoxide or N,N-dimethylformamide. Suitable bases for the reaction include alkali metal hydrides such as sodium hydride; or alkali metal alkoxides such as sodium isopropoxide and potassium tert-butoxide; or alkali metal hydroxides such as potassium hydroxide and sodium hydroxide; or alkali metal carbonates such as potassium carbonate and cesium carbonate; or amide bases such as lithium bis(trimethylsilyl)amide, sodium bis(trimethylsilyl) amide and lithium diisopropylamide; or tertiary amines such as triethylamine and diisopropylethylamine Preferably, a compound of Formula 8 can be prepared by nucleophilic substitution by heating a compound of Formula 1 with a compound of Formula 7A or 7B in a suitable solvent, such as acetonitrile or N,N-dimethylformamide in the presence of a base such as potassium or cesium carbonate, at temperatures ranging from 20 to 110° C., or from 50 to 110° C.

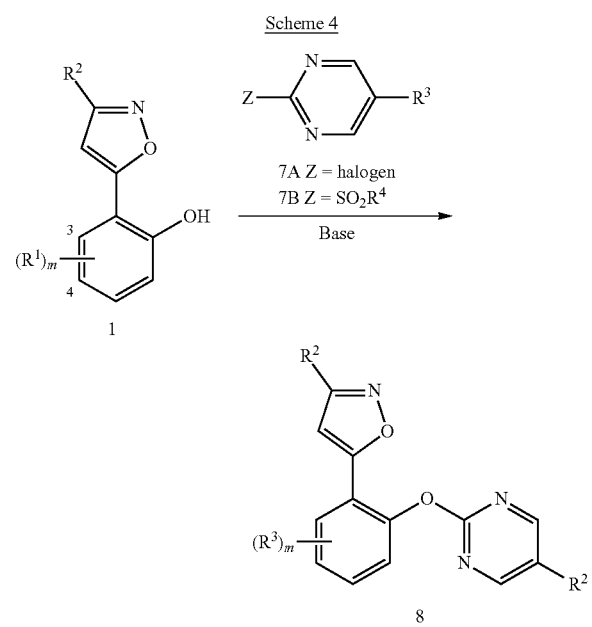

As shown in Schemes 5 and 6, a compound of Formula 7B can be prepared in a telescopic manner. The method comprises treating a compound of Formula 10 and a compound Formula 11 with a halogenating agent, optionally in a suitable solvent, to give an intermediate of Formula 12, which is treated without its isolation with an acid salt of a compound of Formula 13 in the presence of base to provide a compound of Formula 14. A preferred salt of the compound of Formula 13 is the hemisulfate salt (Formula 13A shown in Scheme 5). Suitable halogenating agents include $POCl_3$, $POBr_3$, $SOCl_2$, $SOBr_2$, $(COCl)_2$ or $COCl_2$, preferably $POCl_3$, $SOCl_2$, $(COCl)_2$ or $COCl_2$. When a brominating agent is used, Hal⁻ in Formula 12 is a bromide ion and when a chlorinating agent is used, Hal⁻ in Formula 12 is a chloride ion. Phosphorus oxychloride, $POCl_3$, is a more preferred halogenating agent. Alternatively, the halogenating agent can be pre-prepared as the Vilsmeier-Haack reagent by the reaction of $COCl_2$ with N,N-dimethylformamide. Suitable solvents include N,N-dimethylformamide, dichloroethane, toluene, or acetonitrile. Suitable bases for this reaction include alkali metal alkoxides such as sodium methoxide and sodium isopropoxide; or alkali metal acetates such as sodium acetate and potassium acetate; or tertiary amines such as triethylamine and diisopropylethylamine N,N-dimethylformamide is a preferred compound of Formula 11. In some embodiments, notably when the compound of Formula 11 is N,N-dimethylformamide, an excess of the compound of Formula 11 can be used instead of an additional solvent. The compound of Formula 10 and the halogenating agent can be added to the compound of Formula 11 sequentially in any order, or simultaneously.

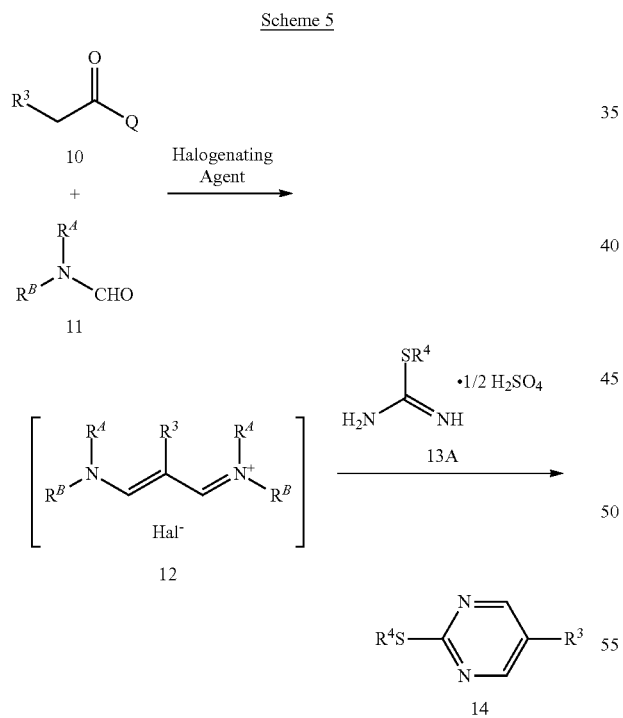

As shown in Scheme 6, an alkylsufonyl pyrimidine compound of Formula 7B can be prepared by oxidizing a compound of Formula 14 with an oxidant such as m-chloroperoxybenzoic acid, sodium periodate, potassium permanganate, potassium peroxymonosulfate (Oxone®) or hydrogen peroxide in a suitable solvent or a mixture of solvents such as water, dichloromethane, methanol, acetonitrile, acetic acid, or ethyl acetate.

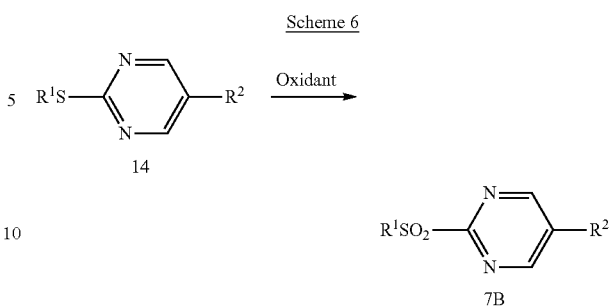

It is recognized that some reagents and reaction conditions described above for preparing compounds of Formulae 1-14 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formulae 1-14. One skilled in the art will also recognize that it may be necessary to perform a combination of the steps illustrated in the above schemes in an order other than that implied by the particular sequence presented to prepare the compounds of Formulae 1-14. One skilled in the art will also recognize that compounds of Formulae 1-14 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight. The abbreviation "h" stands for "hour" or "hours". "HPLC" means high performance liquid chromatography. ¹H NMR spectra are reported in ppm downfield from tetramethylsilane; s is singlet, d is doublet, dd is doublet of doublets, t is triplet and m is multiplet.

Synthesis Example 1

Preparation of 3-chloro-2-[3-(difluoromethyl)isoxazol-5-yl]-phenol

Step A: Preparation of
5-chloro-2-(difluoromethyl)-4H-1-benzopyran-4-one

To a 250-mL round-bottom flask equipped with overhead stirrer, distillation head, and nitrogen inlet were added sodium methoxide (10.8 g, 200 mmol) and N,N-dimethylacetamide (50 mL) at 25° C. A pre-mixed solution of 2,6-dichloroacetophenone (35 g, 181 mmol) and ethyl difluoroacetate (27 g, 218 mmol) in N,N-dimethylacetamide (20 mL) was added into the sodium methoxide slurry dropwise to keep the reaction temperature between 25 and 35° C. After 1 h at 35° C., methanol and ethanol, generated from the reaction, were removed by distillation under reduced pressure. To a separate 1-L round-bottom flask equipped with overhead stirrer, reflux condenser, and nitrogen inlet was added NN-dimethylacetamide (80 mL), which was heated to 150° C. The reaction mixture was added into the hot NN-dimethylacetamide over 2.5 h while keeping the temperature at 150° C. Upon completion as judged by HPLC analysis, the reaction mixture was cooled to 50° C. Water (200 mL) was added into the reactor slowly, and the resulting slurry was cooled to 20° C. slowly and stirred for 1 h. The solid was then collected by filtration, washed with water (100 mL) and dried at ambient temperature to afford 38 g of the crude product. The crude product was treated with activated carbon to remove color impurities and recrystallized from toluene to give 31.7 g of the title compound as a pale yellow solid (76% yield from 2,6-dichloroacetophenone). $^1$H NMR δ 7.79 (t, 1H), 7.70 (dd, 1H), 7.76 (dd, 1H), 7.15-6.89 (t, 1H), 6.68 (s, 1H). M.P.=113° C.

Step B: Preparation of 3-chloro-2-[3-(difluoromethyl)-5-isoxazolyl]-phenol

To a 500 mL jacketed reactor equipped with overhead stirrer and temperature probe were added 5-chloro-2-(difluoromethyl)-4H-1-benzopyran-4-one (i.e. the product of Step A, Synthesis Example 1; 50 g, 217 mmol), hydroxylamine hydrogen chloride salt (18.1 g, 260 mmol), and methanol (150 mL) at ambient temperature. Solid sodium acetate (21.3 g, 260 mmol) was added into the reaction mixture in one portion, and the resulting slurry was stirred overnight. Then, concentrated hydrogen chloride solution (34 g, 325 mmol) was added slowly, and the resulting slurry was stirred for 1 h. Upon completion as judged by HPLC, water (220 mL) was added into the reactor, and the slurry was stirred at ambient temperature for 2 h. The solid was then collected by filtration, washed with 10% methanol in water (150 mL) and dried at ambient temperature to afford 49.1 g of the title compound (93 wt %, 91% yield from 5-chloro-2-(difluoromethyl)-4H-1-benzopyran-4-one). $^1$H NMR δ 10.7 (s, 1H), 7.48-7.22 (t, 1H), 7.40 (t, 1H), 7.09 (d, 1H), 7.05 (s, 1H), 7.01 (d, 1H). M.P.=139.7° C.

Synthesis Example 2

Preparation of 5-chloro-2-(methylthio)-pyrimidine (CAS Number 38275-42-2)

To a 100 mL jacketed reactor equipped with an overhead stirrer, a thermocouple, a recirculating heating and cooling bath, a nitrogen inlet, and a scrubber was added 41 mL of N,N-dimethylformamide, and the reactor was heated to 50° C. Chloroacetyl chloride (10 g, 88.5 mmol) was added dropwise, and the reaction mixture was kept at 50° C. for 1 h. The resulting mixture was then heated to 70° C. followed by the addition of phosphorus oxychloride (13.6 g, 88.5 mmol), dropwise to keep the temperature between 70 and 75° C. The reaction was kept at 70° C. for 4 h, and then cooled to 50° C. S-Methylisothiourea hemisulfate (12.3 g, 88.5 mmol) was added to the reaction mixture, followed by solid sodium methoxide (23.9 g, 443 mmol). The resulting mixture was heated to 60° C. for 2 h, and then cooled to 40° C. Water (60 mL) was added dropwise into the reactor, and the resulting slurry was cooled to 20° C. slowly and stirred for 2 h. The solid was then collected by filtration, washed with water, 20 mL, and dried at ambient temperature to afford the title compound, a compound of Formula 1, (8.5 g, 60% yield from chloroacetyl chloride). $^1$H NMR (400 MHz, DMSO-$d_6$) δ 8.76 (s, 2H), 2.53 (s, 3H). M.P.=61.6° C.

Synthesis Example 3

Alternate Preparation of 5-chloro-2-(methylthio)-pyrimidine (CAS Number 38275-42-2)

To a 100 mL jacketed reactor equipped with an overhead stirrer, a thermocouple, a recirculating heating and cooling bath, a nitrogen inlet, and a scrubber were added Vilsmeier-Haack reagent, 12.3 g (92.9 mmol) and 30 mL of N,N-dimethylformamide. The resulting slurry was then heated to 50° C. Chloroacetyl chloride, 10 g (88.5 mmol), was added dropwise to keep the reaction temperature between 50 and 52° C., and the reaction mixture was kept at 50° C. overnight. The resulting solution was cooled down to ambient temperature and transferred to an addition funnel. Triethylamine, 17.6 g (177 mmol) and 30 mL of N,N-dimethylformamide were added into the reactor, and the mixture was cooled down to 10° C. The solution in additional funnel was then added dropwise while keeping the temperature below 25° C., and S-methylisothiourea hemisulfate, 13.3 g (97.4 mmol) was added in one portion. The resulting reaction mixture was then heated to 70° C. for 4 h, and cooled down to 20° C. Water (100 mL) was added dropwise into the reactor, and the resulting slurry was stirred for 2 h. The solid was then collected by filtration, washed with water, 30 mL×2 times, and dried at room temperature to afford 10.1 g of the title product (99.3 wt %, 72% yield from chloroacetyl chloride). $^1$H NMR (400 MHz, DMSO-$d_6$) δ 8.76 (s, 2H), 2.52 (s, 3H). M.P.=61.6° C.

Synthesis Example 4

Preparation of 5-chloro-2-(methylsulfonyl)-pyrimidine (CAS Number 38275-47-7)

To a 100 mL jacketed reactor equipped with an overhead stirrer, a thermocouple, a recirculating heating and cooling bath, and a nitrogen inlet were added 5-chloro-2-(methylthio)-pyrimidine (i.e. the product of Synthesis Example 2 or 3; 5 g, 31.1 mmol) and sodium tungstate dihydrate (0.52 g, 1.6 mmol) followed by water (15 mL) and ethyl acetate (15 mL) at ambient temperature. The resulting mixture was heated to 60° C., and then 50% aqueous hydrogen peroxide (5.3 g, 77.7 mmol), was added dropwise to maintain the reaction temperature between 60 and 65° C. After 2 h, the reaction was determined to be complete by HPLC. The reaction mixture was cooled to ambient temperature, and excess hydrogen peroxide in the reaction mixture was quenched with sodium bisulfite. The organic layer was then separated, and the aqueous layer was extracted with 15 mL of ethyl acetate. The combined organic layers were concentrated to give a crude product. Crystallization from toluene and heptane provided 5.6 g of the title compound, a compound of Formula 6, (93% yield from 5-chloro-2-(methylthio)-pyrimidine). $^1$H NMR (400 MHz, DMSO-$d_6$) δ 9.24 (s, 2H), 3.42 (s, 3H). M.P.=122° C.

Synthesis Example 5

Preparation of 5-chloro-2-[2-[3-(difluoromethyl)-5-isoxazolyl]-3-chlorophenoxy]-pyrimidine (Alternatively Named 5-chloro-2-[3-chloro-2-[3-(difluoromethyl)-5-isoxazolyl]-phenoxy]-pyrimidine; CAS Number 1801862-02-1)

To a 100 mL nitrogen-flushed glass jacketed reactor equipped with a heating/cooling recirculation bath, nitrogen inlet, temperature probe and overhead stirrer were added 3-chloro-2-[3-(difluoromethyl)-5-isoxazolyl]-phenol (i.e. the product of Step B, Synthesis Example 1; 4.02 g, 96.5 wt %, 15.8 mmol), 5-chloro-2-(methylsulfonyl)-pyrimidine (i.e. the product of Synthesis Example 4; 3.44 g, 97.0 wt %, 17.3 mmol) potassium carbonate (3.27 g, 23.7 mmol) and isopropyl alcohol (12.1 g). The resulting slurry was heated to 65° C. for 1 h and upon completion as judged by HPLC analysis, water (12.1 g) was added over 5 minutes. The reaction mixture was cooled to 54° C., the two liquid phases were allowed to separate, and the aqueous phase was removed. Upon cooling the organic solution to 0° C., a solid crystallized from the isopropyl alcohol. The solid was collected by filtration, washed with pre-cooled isopropyl alcohol/water mixture (4/1 v/v, 3.5 g), and dried under vacuum at 60° C. to afford of the title compound (4.62 g, 99.4 wt %, 81.2% yield), a compound of Formula 8. $^1$H NMR (400 MHz, CDCl$_3$) δ 8.44 (s, 2H), 7.47-7.55 (m, 2H), 7.22 (dd, 1H), 6.61-6.87 (t, 1H), 6.70 (s, 1H). M.P.=66.5° C.

By the procedures described herein together with methods known in the art, the following compounds can be prepared using the claimed methods. The following abbreviations are used in the Tables which follow: Et means ethyl (CH$_2$CH$_3$), Pr means propyl, i-Pr means isopropyl, and Bu means butyl.

Each of the following Tables is constructed in the same manner as Table 1 above, except that the header row in Table 1 (i.e. "m is 0 (i.e. $R^1$ is absent)") is replaced with the respective header row shown below. For example, the first entry in Table 2 is a compound of Formula 4 wherein m is 1, $R^1$ is 3-F, X is Cl and $R^2$ is CN. The remainder of Table 2 is constructed in the same way, and hence the remainder of Tables 3 through 59 are constructed the same way.

| Table | Header Row | Table | Header Row |
|---|---|---|---|
| 2 | m is 1, and $R^1$ is 3-F | 3 | m is 1, and $R^1$ is 4-F |
| 4 | m is 1, and $R^1$ is 3-Cl | 5 | m is 1, and $R^1$ is 4-Cl |
| 6 | m is 1, and $R^1$ is 3-Br | 7 | m is 1, and $R^1$ is 4-Br |
| 8 | m is 1, and $R^1$ is 3-I | 9 | m is 1, and $R^1$ is 4-I |
| 10 | m is 1, and $R^1$ is 3-CN | 11 | m is 1, and $R^1$ is 4-CN |
| 12 | m is 1, and $R^1$ is 3-Me | 13 | m is 1, and $R^1$ is 4-Me |
| 14 | m is 1, and $R^1$ is 3-Et | 15 | m is 1, and $R^1$ is 4-Et |
| 16 | m is 1, and $R^1$ is 3-Pr | 17 | m is 1, and $R^1$ is 4-Pr |
| 18 | m is 1, and $R^1$ is 3-CF$_3$ | 19 | m is 1, and $R^1$ is 4-CF$_3$ |
| 20 | m is 1, and $R^1$ is 3-CH$_2$F | 21 | m is 1, and $R^1$ is 4-CH$_2$F |
| 22 | m is 1, and $R^1$ is 3-CHF$_2$ | 23 | m is 1, and $R^1$ is 4-CHF$_2$ |
| 24 | m is 1, and $R^1$ is 3-CH$_2$CF$_3$ | 25 | m is 1, and $R^1$ is 4-CH$_2$CF$_3$ |
| 26 | m is 1, and $R^1$ is 3-CF$_2$CF$_3$ | 27 | m is 1, and $R^1$ is 4-CF$_2$CF$_3$ |
| 28 | m is 2, and $R^1$ is 3,4-di-F | 29 | m is 2, and $R^1$ is 3,4-di-Cl |
| 30 | m is 2, and $R^1$ is 3-Cl, 4-F | 31 | m is 2, and $R^1$ is 3-F, 4-Cl |

TABLE 1

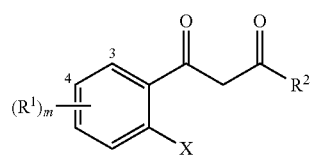

4 wherein m is 0 (i.e. $R^1$ is absent)

| X | $R^2$ | X | $R^2$ | X | $R^2$ | X | $R^2$ |
|---|---|---|---|---|---|---|---|
| Cl | CN | Br | CN | I | CN | Cl | CH$_2$CH$_2$CF$_3$ |
| Cl | CH$_3$ | Br | CH$_3$ | I | CH$_3$ | Cl | CH$_2$CHFCHF$_2$ |
| Cl | CHF$_2$ | Br | CHF$_2$ | I | CHF$_2$ | Cl | CH$_2$CH$_2$CHCl$_2$ |
| Cl | CH$_2$F | Br | CH$_2$F | I | CH$_2$F | Cl | CH$_2$CH$_2$CCl$_3$ |
| Cl | CF$_3$ | Br | CF$_3$ | I | CF$_3$ | Cl | CF$_2$CF$_2$CF$_3$ |
| Cl | CH$_2$CF$_3$ | Br | CH$_2$CF$_3$ | I | CH$_2$CF$_3$ | Cl | CF$_2$CF$_2$CF$_2$CF$_3$ |
| Cl | CF$_2$CF$_3$ | Br | CF$_2$CF$_3$ | I | CF$_2$CF$_3$ | Cl | CH$_2$CH$_2$CH$_2$CF$_3$ |
| Cl | CHFCF$_3$ | Br | CHFCF$_3$ | I | CHFCF$_3$ | Br | CH$_2$CH$_2$CF$_3$ |
| Cl | Et | Br | Et | I | Et | Br | CH$_2$CHFCHF$_2$ |
| Cl | CHFCHF$_2$ | Br | CHFCHF$_2$ | I | CHFCHF$_2$ | Br | CH$_2$CH$_2$CHCl$_2$ |
| Cl | CH$_2$Cl | Br | CH$_2$Cl | I | CH$_2$Cl | Br | CH$_2$CH$_2$CCl$_3$ |
| Cl | CHCl$_2$ | Br | CHCl$_2$ | I | CHCl$_2$ | Br | CF$_2$CF$_2$CF$_3$ |
| Cl | Pr | Br | Pr | I | Pr | Br | CF$_2$CF$_2$CF$_2$CF$_3$ |
| Cl | i-Pr | Br | i-Pr | I | i-Pr | Br | CH$_2$CH$_2$CH$_2$CF$_3$ |
| Cl | Bu | Br | Bu | I | Bu | I | CH$_2$CH$_2$CF$_3$ |
| Cl | CCl$_2$CF$_3$ | Br | CCl$_2$CF$_3$ | I | CCl$_2$CF$_3$ | I | CH$_2$CH$_2$CHCl$_2$ |
| Cl | CH$_2$CCl$_3$ | Br | CH$_2$CCl$_3$ | I | CH$_2$CCl$_3$ | I | CH$_2$CH$_2$CCl$_3$ |
| Cl | CH$_2$CH$_2$F | Br | CH$_2$CH$_2$F | I | CH$_2$CH$_2$F | I | CF$_2$CF$_2$CF$_3$ |
| Cl | CH$_2$CH$_2$Cl | Br | CH$_2$CH$_2$Cl | I | CH$_2$CH$_2$Cl | I | CH$_2$CHFCHF$_2$ |
| Cl | CH$_2$CHCl$_2$ | Br | CH$_2$CHCl$_2$ | Br | CH$_2$CHCl$_2$ | I | CF$_2$CF$_2$CF$_2$CF$_3$ |
| Cl | CHClCHCl$_2$ | Br | CHClCHCl$_2$ | I | CHClCHCl$_2$ | I | CH$_2$CH$_2$CH$_2$CF$_3$ |

-continued

| Table | Header Row | Table | Header Row |
|---|---|---|---|
| 32 | m is 2, and $R^1$ is 3-Cl, 4-Me | 33 | m is 2, and $R^1$ is 3-F, 4-Me |
| 34 | m is 2, and $R^1$ is 3-Me, 4-F | 35 | m is 2, and $R^1$ is 3-Me, 4-Cl |

TABLE 36

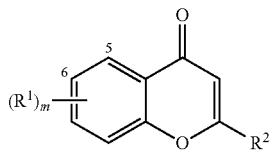

wherein m is 0 (i.e. $R^1$ is absent)

| $R^2$ | $R^2$ | $R^2$ | $R^2$ |
|---|---|---|---|
| CN | Et | CHFCHF$_2$ | CF$_2$CF$_2$CF$_3$ |
| CHF$_2$ | Pr | CCl$_2$CF$_3$ | CH$_2$CH$_2$CF$_3$ |
| CH$_2$F | i-Pr | CH$_2$CCl$_3$ | CH$_2$CHFCHF$_2$ |
| CF$_3$ | Bu | CHClCHCl$_2$ | CH$_2$CH$_2$CHCl$_2$ |
| CH$_2$Cl | CH$_2$CF$_3$ | CH$_2$CHCl$_2$ | CH$_2$CH$_2$CCl$_3$ |
| CHCl$_2$ | CF$_2$CF$_3$ | CH$_2$CH$_2$Cl | CF$_2$CF$_2$CF$_2$CF$_3$ |
| CH$_3$ | CHFCF$_3$ | CH$_2$CH$_2$F | CH$_2$CH$_2$CH$_2$CF$_3$ |

Each of the following Tables is constructed in the same manner as Table 36 above, except that the header row in Table 36 (i.e. "m is 0 (i.e. $R^1$ is absent)") is replaced with the respective header row shown below. For example, the first entry in Table 37 is a compound of Formula 5 wherein m is 1, $R^1$ is 5-F and $R^2$ is CN. The remainder of Table 37 is constructed in the same way, and hence the remainder of Tables 38 through 70 are constructed the same way.

| Table | Header Row | Table | Header Row |
|---|---|---|---|
| 37 | m is 1, and $R^1$ is 5-F | 38 | m is 1, and $R^1$ is 6-F |
| 39 | m is 1, and $R^1$ is 5-Cl | 40 | m is 1, and $R^1$ is 6-Cl |
| 41 | m is 1, and $R^1$ is 5-Br | 42 | m is 1, and $R^1$ is 6-Br |
| 43 | m is 1, and $R^1$ is 5-I | 44 | m is 1, and $R^1$ is 6-I |
| 45 | m is 1, and $R^1$ is 5-CN | 46 | m is 1, and $R^1$ is 6-CN |
| 47 | m is 1, and $R^1$ is 5-Me | 48 | m is 1, and $R^1$ is 6-Me |
| 49 | m is 1, and $R^1$ is 5-Et | 50 | m is 1, and $R^1$ is 6-Et |
| 51 | m is 1, and $R^1$ is 5-Pr | 52 | m is 1, and $R^1$ is 6-Pr |
| 53 | m is 1, and $R^1$ is 5-CF$_3$ | 54 | m is 1, and $R^1$ is 6-CF$_3$ |
| 55 | m is 1, and $R^1$ is 5-CH$_2$F | 56 | m is 1, and $R^1$ is 6-CH$_2$F |
| 57 | m is 1, and $R^1$ is 5-CHF$_2$ | 58 | m is 1, and $R^1$ is 6-CHF$_2$ |
| 59 | m is 1, and $R^1$ is 5-CH$_2$CF$_3$ | 60 | m is 1, and $R^1$ is 6-CH$_2$CF$_3$ |
| 61 | m is 1, and $R^1$ is 5-CF$_2$CF$_3$ | 62 | m is 1, and $R^1$ is 6-CF$_2$CF$_3$ |
| 63 | m is 2, and $R^1$ is 5,6-di-F | 64 | m is 2, and $R^1$ is 5,6-di-Cl |
| 65 | m is 2, and $R^1$ is 5-Cl, 6-F | 66 | m is 2, and $R^1$ is 5-F, 6-Cl |
| 67 | m is 2, and $R^1$ is 5-Cl, 6-Me | 68 | m is 2, and $R^1$ is 5-F, 6-Me |
| 69 | m is 2, and $R^1$ is 5-Me, 6-F | 70 | m is 2, and $R^1$ is 5-Me, 6-Cl |

TABLE 71

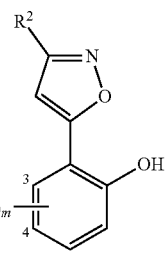

wherein m is 0 (i.e. $R^1$ is absent)

| $R^2$ | $R^2$ | $R^2$ | $R^2$ |
|---|---|---|---|
| CN | Et | CHFCHF$_2$ | CH$_2$CH$_2$CF$_3$ |
| CHF$_2$ | Pr | CCl$_2$CF$_3$ | CH$_2$CHFCHF$_2$ |
| CH$_2$F | i-Pr | CH$_2$CCl$_3$ | CH$_2$CH$_2$CHCl$_2$ |
| CF$_3$ | Bu | CHClCHCl$_2$ | CH$_2$CH$_2$CHCl$_2$ |
| CH$_2$Cl | CH$_2$CF$_3$ | CH$_2$CHCl$_2$ | CH$_2$CH$_2$CCl$_3$ |
| CHCl$_2$ | CF$_2$CF$_3$ | CH$_2$CH$_2$Cl | CF$_2$CF$_2$CF$_2$CF$_3$ |
| CH$_3$ | CHFCF$_3$ | CF$_2$CF$_2$CF$_3$ | CH$_2$CH$_2$CH$_2$CF$_3$ |

Each of the following Tables is constructed in the same manner as Table 71 above, except that the header row in Table 71 (i.e. "m is 0 (i.e. $R^1$ is absent)") is replaced with the respective header row shown below. For example, the first entry in Table 72 is a compound of Formula 1 wherein m is 1, $R^1$ is 3-F and $R^2$ is CN. The remainder of Table 72 is constructed in the same way, and hence the remainder of Tables 73 through 105 are constructed the same way.

| Table | Header Row | Table | Header Row |
|---|---|---|---|
| 72 | m is 1, and $R^1$ is 3-F | 73 | m is 1, and $R^1$ is 4-F |
| 74 | m is 1, and $R^1$ is 3-Cl | 75 | m is 1, and $R^1$ is 4-Cl |
| 76 | m is 1, and $R^1$ is 3-Br | 77 | m is 1, and $R^1$ is 4-Br |
| 78 | m is 1, and $R^1$ is 3-I | 79 | m is 1, and $R^1$ is 4-I |
| 80 | m is 1, and $R^1$ is 3-CN | 81 | m is 1, and $R^1$ is 4-CN |
| 82 | m is 1, and $R^1$ is 3-Me | 83 | m is 1, and $R^1$ is 4-Me |
| 84 | m is 1, and $R^1$ is 3-Et | 85 | m is 1, and $R^1$ is 4-Et |
| 86 | m is 1, and $R^1$ is 3-Pr | 87 | m is 1, and $R^1$ is 4-Pr |
| 88 | m is 1, and $R^1$ is 3-CF$_3$ | 89 | m is 1, and $R^1$ is 4-CF$_3$ |
| 90 | m is 1, and $R^1$ is 3-CH$_2$F | 91 | m is 1, and $R^1$ is 4-CH$_2$F |
| 92 | m is 1, and $R^1$ is 3-CHF$_2$ | 93 | m is 1, and $R^1$ is 4-CHF$_2$ |
| 94 | m is 1, and $R^1$ is 3-CH$_2$CF$_3$ | 95 | m is 1, and $R^1$ is 4-CH$_2$CF$_3$ |
| 96 | m is 1, and $R^1$ is 3-CF$_2$CF$_3$ | 97 | m is 1, and $R^1$ is 4-CF$_2$CF$_3$ |
| 98 | m is 2, and $R^1$ is 3,4-di-F | 99 | m is 2, and $R^1$ is 3,4-di-Cl |
| 100 | m is 2, and $R^1$ is 3-Cl, 4-F | 101 | m is 2, and $R^1$ is 3-F, 4-Cl |
| 102 | m is 2, and $R^1$ is 3-Cl, 4-Me | 103 | m is 2, and $R^1$ is 3-F, 4-Me |
| 104 | m is 2, and $R^1$ is 3-Me, 4-F | 105 | m is 2, and $R^1$ is 3-Me, 4-Cl |

TABLE 106

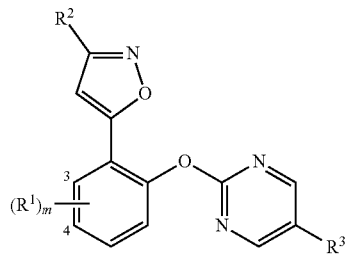

8 wherein m is 0 (i.e. $R^1$ is absent)

| $R^2$ | $R^3$ | $R^2$ | $R^3$ | $R^2$ | $R^3$ | $R^2$ | $R^3$ |
|---|---|---|---|---|---|---|---|
| CN | Cl | CN | Br | CN | $CH_3$ | CN | $CF_3$ |
| $CH_3$ | Cl | $CH_3$ | Br | $CH_3$ | $CH_3$ | $CH_3$ | $CF_3$ |
| $CHF_2$ | Cl | $CHF_2$ | Br | $CHF_2$ | $CH_3$ | $CHF_2$ | $CF_3$ |
| $CH_2F$ | Cl | $CH_2F$ | Br | $CH_2F$ | $CH_3$ | $CH_2F$ | $CF_3$ |
| $CF_3$ | Cl | $CF_3$ | Br | $CF_3$ | $CH_3$ | $CF_3$ | $CF_3$ |
| $CH_2CF_3$ | Cl | $CH_2CF_3$ | Br | $CH_2CF_3$ | $CH_3$ | $CH_2CF_3$ | $CF_3$ |
| $CF_2CF_3$ | Cl | $CF_2CF_3$ | Br | $CF_2CF_3$ | $CH_3$ | $CF_2CF_3$ | $CF_3$ |
| $CHFCF_3$ | Cl | $CHFCF_3$ | Br | $CHFCF_3$ | $CH_3$ | $CHFCF_3$ | $CF_3$ |
| Et | Cl | Et | Br | Et | $CH_3$ | Et | $CF_3$ |
| $CH_2CF_3$ | Cl | $CH_2CF_3$ | Br | $CH_2CF_3$ | $CH_3$ | $CH_2CF_3$ | $CF_3$ |
| $CHFCHF_2$ | Cl | $CHFCHF_2$ | Br | $CHFCHF_2$ | $CH_3$ | $CHFCHF_2$ | $CF_3$ |
| $CH_2Cl$ | Cl | $CH_2Cl$ | Br | $CH_2Cl$ | $CH_3$ | $CH_2Cl$ | $CF_3$ |
| $CHCl_2$ | Cl | $CHCl_2$ | Br | $CHCl_2$ | $CH_3$ | $CHCl_2$ | $CF_3$ |
| Pr | Cl | Pr | Br | Pr | $CH_3$ | Pr | $CF_3$ |
| i-Pr | Cl | i-Pr | Br | i-Pr | $CH_3$ | Bu | $CF_3$ |
| Bu | Cl | Bu | Br | Bu | $CH_3$ | i-Pr | $CF_3$ |
| $CCl_2CF_3$ | Cl | $CCl_2CF_3$ | Br | $CCl_2CF_3$ | $CH_3$ | $CCl_2CF_3$ | $CF_3$ |
| $CH_2CCl_3$ | Cl | $CH_2CCl_3$ | Br | $CH_2CCl_3$ | $CH_3$ | $CH_2CCl_3$ | $CF_3$ |
| $CHClCHCl_2$ | Cl | $CHClCHCl_2$ | Br | $CHClCHCl_2$ | $CH_3$ | $CHClCHCl_2$ | $CF_3$ |
| $CH_2CHCl_2$ | Cl | $CH_2CHCl_2$ | Br | $CH_2CHCl_2$ | $CH_3$ | $CH_2CHCl_2$ | $CF_3$ |
| $CH_2CH_2Cl$ | Cl | $CH_2CH_2Cl$ | Br | $CH_2CH_2Cl$ | $CH_3$ | $CH_2CH_2Cl$ | $CF_3$ |
| $CH_2CH_2CF_3$ | Cl | $CH_2CH_2CF_3$ | Br | $CH_2CH_2CF_3$ | $CH_3$ | $CH_2CH_2CF_3$ | $CF_3$ |
| $CH_2CHFCHF_2$ | Cl | $CH_2CHFCHF_2$ | Br | $CH_2CHFCHF_2$ | $CH_3$ | $CH_2CHFCHF_2$ | $CF_3$ |
| $CH_2CH_2CHCl_2$ | Cl | $CH_2CH_2CHCl_2$ | Br | $CH_2CH_2CHCl_2$ | $CH_3$ | $CH_2CH_2CHCl_2$ | $CF_3$ |
| $CH_2CH_2CCl_3$ | Cl | $CH_2CH_2CCl_3$ | Br | $CH_2CH_2CCl_3$ | $CH_3$ | $CH_2CH_2CCl_3$ | $CF_3$ |
| $CF_2CF_2CF_3$ | Cl | $CF_2CF_2CF_3$ | Br | $CF_2CF_2CF_3$ | $CH_3$ | $CF_2CF_2CF_3$ | $CF_3$ |
| $CF_2CF_2CF_2CF_3$ | Cl | $CF_2CF_2CF_2CF_3$ | Br | $CF_2CF_2CF_2CF_3$ | $CH_3$ | $CF_2CF_2CF_2CF_3$ | $CF_3$ |
| $CH_2CH_2CH_2CF_3$ | Cl | $CH_2CH_2CH_2CF_3$ | Br | $CH_2CH_2CH_2CF_3$ | $CH_3$ | $CH_2CH_2CH_2CF_3$ | $CF_3$ |

Each of the following Tables is constructed in the same manner as Table 106 above, except that the header row in Table 106 (i.e. "m is 0 (i.e. $R^1$ is absent)") is replaced with the respective header row shown below. For example, the first entry in Table 107 is a compound of Formula 8 wherein m is 1, $R^1$ is 3-F, $R^2$ is CN and $R^3$ is Cl. The remainder of Table 107 is constructed in the same way, and hence the remainder of Tables 108 through 140 are constructed the same way.

| Table | Header Row | Table | Header Row |
|---|---|---|---|
| 107 | m is 1, and $R^1$ is 3-F | 108 | m is 1, and $R^1$ is 4-F |
| 109 | m is 1, and $R^1$ is 3-Cl | 110 | m is 1, and $R^1$ is 4-Cl |
| 111 | m is 1, and $R^1$ is 3-Br | 112 | m is 1, and $R^1$ is 4-Br |
| 113 | m is 1, and $R^1$ is 3-I | 114 | m is 1, and $R^1$ is 4-I |
| 115 | m is 1, and $R^1$ is 3-CN | 116 | m is 1, and $R^1$ is 4-CN |
| 117 | m is 1, and $R^1$ is 3-Me | 118 | m is 1, and $R^1$ is 4-Me |
| 119 | m is 1, and $R^1$ is 3-Et | 120 | m is 1, and $R^1$ is 4-Et |
| 121 | m is 1, and $R^1$ is 3-Pr | 122 | m is 1, and $R^1$ is 4-Pr |
| 123 | m is 1, and $R^1$ is 3-$CF_3$ | 124 | m is 1, and $R^1$ is 4-$CF_3$ |
| 125 | m is 1, and $R^1$ is 3-$CH_2F$ | 126 | m is 1, and $R^1$ is 4-$CH_2F$ |
| 127 | m is 1, and $R^1$ is 3-$CHF_2$ | 128 | m is 1, and $R^1$ is 4-$CHF_2$ |
| 129 | m is 1, and $R^1$ is 3-$CH_2CF_3$ | 130 | m is 1, and $R^1$ is 4-$CH_2CF_3$ |
| 131 | m is 1, and $R^1$ is 3-$CF_2CF_3$ | 132 | m is 1, and $R^1$ is 4-$CF_2CF_3$ |
| 133 | m is 2, and $R^1$ is 3,4-di-F | 134 | m is 2, and $R^1$ is 3,4-di-Cl |
| 135 | m is 2, and $R^1$ is 3-Cl, 4-F | 136 | m is 2, and $R^1$ is 3-F, 4-Cl |

-continued

| Table | Header Row | Table | Header Row |
|---|---|---|---|
| 137 | m is 2, and $R^1$ is 3-Cl, 4-Me | 138 | m is 2, and $R^1$ is 3-F, 4-Me |
| 139 | m is 2, and $R^1$ is 3-Me, 4-F | 140 | m is 2, and $R^1$ is 3-Me, 4-Cl |

What is claimed is:

1. A method for preparing a compound of Formula 1

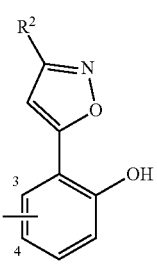

1 wherein
each $R^1$ is independently halogen, cyano, $C_1$-$C_4$ alkyl or $C_1$-$C_4$ haloalkyl;
$R^2$ is cyano, $C_1$-$C_4$ alkyl or $C_1$-$C_4$ haloalkyl; and
m is 0, 1, 2 or 3;

the method comprising treating a compound of Formula 2

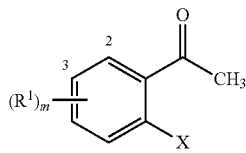

wherein
each $R^1$ is independently halogen, cyano, $C_1$-$C_4$ alkyl or $C_1$-$C_4$ haloalkyl;
m is 0, 1, 2 or 3; and
X is halogen;
with a compound of Formula 3

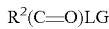

wherein
$R^2$ is cyano, $C_1$-$C_4$ alkyl or $C_1$-$C_4$ haloalkyl; and
LG is chloro, $C_1$-$C_4$ alkoxy or —O(C=O)$R^2$
in the presence of an alkali metal base to provide a compound of Formula 4 or an alkali metal salt thereof

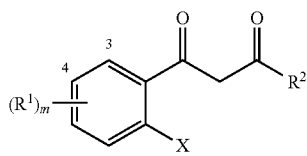

wherein
each $R^1$ is independently halogen, cyano, $C_1$-$C_4$ alkyl or $C_1$-$C_4$ haloalkyl;
$R^2$ is cyano, $C_1$-$C_4$ alkyl or $C_1$-$C_4$ haloalkyl;
m is 0, 1, 2 or 3; and
X is halogen;
heating the compound of Formula 4 or the alkali metal salt thereof to provide a compound of Formula 5

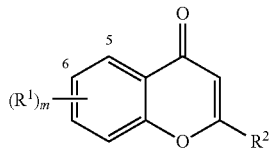

wherein
each $R^1$ is independently halogen, cyano, $C_1$-$C_4$ alkyl or $C_1$-$C_4$ haloalkyl;
$R^2$ is cyano, $C_1$-$C_4$ alkyl or $C_1$-$C_4$ haloalkyl; and
m is 0, 1, 2 or 3;
treating the compound of Formula 5 with a hydroxylamine salt to provide a compound of Formula 6

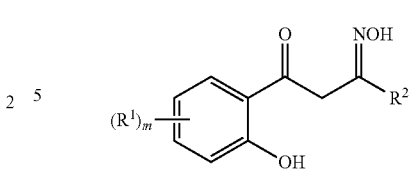

wherein
each $R^1$ is independently halogen, cyano, $C_1$-$C_4$ alkyl or $C_1$-$C_4$ haloalkyl;
$R^2$ is cyano, $C_1$-$C_4$ alkyl or $C_1$-$C_4$ haloalkyl; and
m is 0, 1, 2 or 3; and
treating the compound of Formula 6 with acid.

2. The method of claim 1 wherein $R^2$ is $C_1$-$C_4$ haloalkyl; and m is 0, 1 or 2.

3. The method of claim 2 wherein each $R^1$ is independently halogen or cyano; and $R^2$ is $C_1$-$C_2$ fluoroalkyl.

4. The method of claim 3 wherein
$R^1$ is halogen;
$R^2$ is $C_1$ fluoroalkyl;
m is 1; and
$R^1$ is attached to the remainder of Formula 1 at the 3-position.

5. The method of claim 4 wherein $R^1$ is chlorine; and $R^2$ is $CHF_2$.

6. The method of claim 1 wherein the compound of Formula 2 is prepared by treating a compound of Formula 9

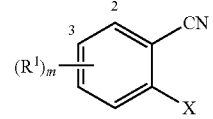

wherein
each $R^1$ is independently halogen, cyano, $C_1$-$C_4$ alkyl or $C_1$-$C_4$ haloalkyl;
X is halogen; and
m is 0, 1, 2 or 3;
with a methyl magnesium halide followed by treatment with water or aqueous acid.

7. The method of claim 1 further comprising treating the compound of Formula 1 with a compound of Formula 7

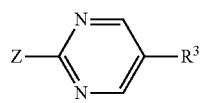

wherein
Z is halogen or $SO_2R^4$;
$R^3$ is halogen, $C_1$-$C_4$ alkyl or $C_1$-$C_4$ haloalkyl; and
$R^4$ is $C_1$-$C_4$ alkyl
in the presence of a second base to provide a compound of Formula 8

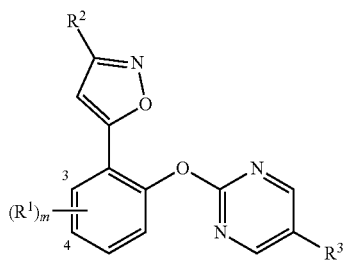

wherein
each R$^1$ is independently halogen, cyano, C$_1$-C$_4$ alkyl or C$_1$-C$_4$ haloalkyl;
R$^2$ is cyano, C$_1$-C$_4$ alkyl or C$_1$-C$_4$ haloalkyl;
R$^3$ is halogen, C$_1$-C$_4$ alkyl or C$_1$-C$_4$ haloalkyl; and
m is 0, 1, 2 or 3.

8. The method of claim 7 wherein R$^3$ is chlorine.

9. The method of claim 7 wherein Z is SO$_2$R$^4$.

10. The method of claim 9 wherein the compound of Formula 7 is prepared by treating a compound of Formula 10

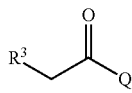

wherein
R$^3$ is halogen, C$_1$-C$_4$ alkyl or C$_1$-C$_4$ haloalkyl; and
Q is Cl or OH
in the presence of a halogenating agent and a compound of Formula 11

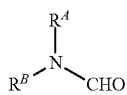

wherein
R$^A$ and R$^B$ are each independently C$_1$-C$_4$ alkyl; or
R$^A$ and R$^B$ are taken together to be —(CH$_2$)$_4$—, —(CH$_2$)$_5$— or —CH$_2$CH$_2$OCH$_2$CH$_2$— to provide an intermediate of Formula 12

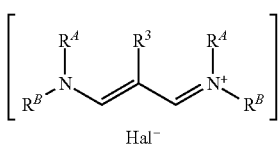

wherein
R$^3$ is halogen, C$_1$-C$_4$ alkyl or C$_1$-C$_4$ haloalkyl; and
R$^A$ and R$^B$ are each independently C$_1$-C$_4$ alkyl; or
R$^A$ and R$^B$ are taken together to be —(CH$_2$)$_4$—, —(CH$_2$)$_5$— or —CH$_2$CH$_2$OCH$_2$CH$_2$—; and
Hal$^-$ is chloride or bromide ion;

treating the intermediate of Formula 12 with an acid salt of a compound of Formula 13

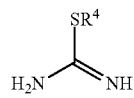

wherein R$^4$ is C$_1$-C$_4$ alkyl
in the presence of a base to provide a compound of Formula 14

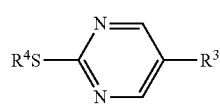

wherein
R$^3$ is halogen, C$_1$-C$_4$ alkyl or C$_1$-C$_4$ haloalkyl;
R$^4$ is C$_1$-C$_4$ alkyl; and
treating the compound of Formula 14 with an oxidant.

11. The method of claim 7 wherein the compound of Formula 8 is the compound of Formula 8A

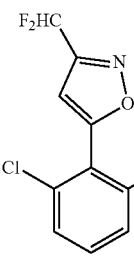

12. A method for preparing a compound of Formula 8

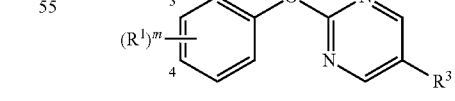

wherein
each R$^1$ is independently halogen, cyano, C$_1$-C$_4$ alkyl or C$_1$-C$_4$ haloalkyl;
R$^2$ is cyano, C$_1$-C$_4$ alkyl or C$_1$-C$_4$ haloalkyl;
R$^3$ is halogen, C$_1$-C$_4$ alkyl or C$_1$-C$_4$ haloalkyl; and
m is 0, 1, 2 or 3;

the method comprising
treating a compound of Formula 2

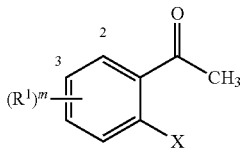

wherein
each $R^1$ is independently halogen, cyano, $C_1$-$C_4$ alkyl or $C_1$-$C_4$ haloalkyl;
m is 0, 1, 2 or 3; and
X is halogen;
with a compound of Formula 3

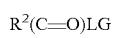   3 wherein
$R^2$ is cyano, $C_1$-$C_4$ alkyl or $C_1$-$C_4$ haloalkyl; and
LG is chloro, $C_1$-$C_4$ alkoxy or —O(C=O)$R^2$
in the presence of a base to provide a salt of a compound of Formula 4

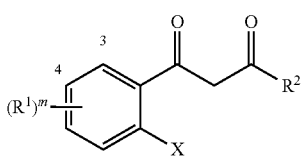

wherein
each $R^1$ is independently halogen, cyano, $C_1$-$C_4$ alkyl or $C_1$-$C_4$ haloalkyl;
$R^2$ is cyano, $C_1$-$C_4$ alkyl or $C_1$-$C_4$ haloalkyl;
m is 0, 1, 2 or 3; and
X is halogen;
heating the salt of the compound of Formula 4 to provide a compound of Formula 5

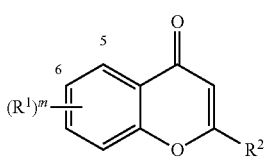

wherein
each $R^1$ is independently halogen, cyano, $C_1$-$C_4$ alkyl or $C_1$-$C_4$ haloalkyl;
$R^2$ is cyano, $C_1$-$C_4$ alkyl or $C_1$-$C_4$ haloalkyl; and
m is 0, 1, 2 or 3;
treating the compound of Formula 5 with a hydroxylamine salt to provide a compound of Formula 6

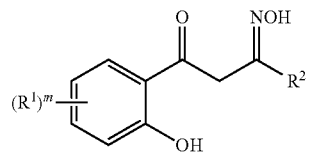

wherein
each $R^1$ is independently halogen, cyano, $C_1$-$C_4$ alkyl or $C_1$-$C_4$ haloalkyl;
$R^2$ is cyano, $C_1$-$C_4$ alkyl or $C_1$-$C_4$ haloalkyl; and
m is 0, 1, 2 or 3;
treating the compound of Formula 6 with acid to provide a compound of Formula 1

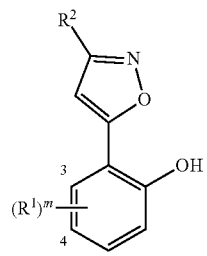

wherein
each $R^1$ is independently halogen, cyano, $C_1$-$C_4$ alkyl or $C_1$-$C_4$ haloalkyl;
$R^2$ is cyano, $C_1$-$C_4$ alkyl or $C_1$-$C_4$ haloalkyl; and
m is 0, 1, 2 or 3; and
treating the compound of Formula 1 with a compound of Formula 7

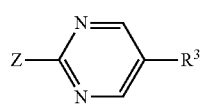

wherein
Z is halogen or $SO_2R^4$;
$R^3$ is halogen, $C_1$-$C_4$ alkyl or $C_1$-$C_4$ haloalkyl;
$R^4$ is $C_1$-$C_4$ alkyl
in the presence of a second base.

13. The method of claim 12 wherein the compound of Formula 2 is prepared by treating a compound of Formula 9

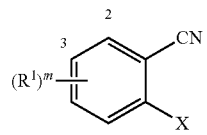

wherein
each $R^1$ is independently halogen, cyano, $C_1$-$C_4$ alkyl or $C_1$-$C_4$ haloalkyl;
X is halogen;
and
m is 0, 1, 2 or 3;

with a methyl magnesium halide followed by treatment with water or aqueous acid.

14. The method of claim 12 wherein Z is $SO_2R^4$.

15. The method of claim 14 wherein the compound of Formula 7 is prepared by treating a compound of Formula 10

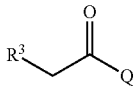

10 wherein
$R^3$ is halogen, $C_1$-$C_4$ alkyl or $C_1$-$C_4$ haloalkyl; and
Q is Cl or OH
in the presence of a halogenating agent and a compound of Formula 11

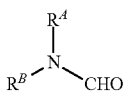

11 wherein
$R^A$ and $R^B$ are each independently $C_1$-$C_4$ alkyl; or
$R^A$ and $R^B$ are taken together to be —(CH$_2$)$_4$—, —(CH$_2$)$_5$— or —CH$_2$CH$_2$OCH$_2$CH$_2$— to provide an intermediate of Formula 12

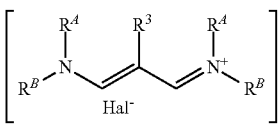

12 wherein
$R^3$ is halogen, $C_1$-$C_4$ alkyl or $C_1$-$C_4$ haloalkyl; and
$R^A$ and $R^B$ are each independently $C_1$-$C_4$ alkyl; or
$R^A$ and $R^B$ are taken together to be —(CH$_2$)$_4$—, —(CH$_2$)$_5$— or —CH$_2$CH$_2$OCH$_2$CH$_2$—; and
Hal$^-$ is chloride or bromide ion;
treating the intermediate of Formula 12 with an acid salt of a compound of Formula 13

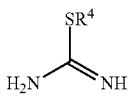

13 wherein $R^4$ is $C_1$-$C_4$ alkyl in the presence of a base to provide a compound of Formula 14

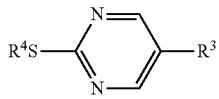

14 wherein
$R^3$ is halogen, $C_1$-$C_4$ alkyl or $C_1$-$C_4$ haloalkyl;
$R^4$ is $C_1$-$C_4$ alkyl; and
treating the compound of Formula 14 with an oxidant.

16. The method of claim 12 wherein the compound of Formula 8 is the compound of Formula 8A

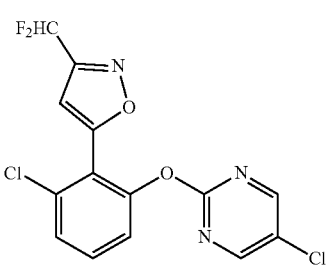

8A

17. A compound of Formula 5A

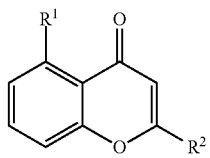

5A wherein
$R^1$ is halogen, cyano, $C_1$-$C_4$ alkyl or $C_1$-$C_4$ haloalkyl; and
$R^2$ is $C_1$-$C_2$ haloalkyl; wherein when $R^1$ is fluoro, $R^2$ is other than trifluoromethyl.

18. The compound of claim 17 wherein $R^2$ is $C_1$-$C_2$ fluoroalkyl.

19. The compound of claim 18 wherein $R^1$ is halogen; and $R^2$ is $C_1$ fluoroalkyl.

20. The compound of claim 19 wherein $R^1$ is chlorine; and $R^2$ is $CF_2$.

* * * * *